United States Patent [19]

Nargund et al.

[11] Patent Number: 5,656,606

[45] Date of Patent: Aug. 12, 1997

[54] CAMPHOR COMPOUNDS PROMOTE RELEASE OF GROWTH HORMONE

[75] Inventors: Ravi Nargund, East Brunswick; Arthur A. Patchett, Westfield, both of N.J.

[73] Assignee: Merck & Co., Inc., Rahway, N.J.

[21] Appl. No.: 390,328

[22] Filed: Feb. 17, 1995

[51] Int. Cl.$^6$ ............ A61K 31/16; A61K 31/445; A61K 31/495; A61K 38/22

[52] U.S. Cl. ............ 514/21; 514/12; 514/255; 514/278; 514/319; 514/325; 544/383; 544/391; 546/17; 546/205

[58] Field of Search ............ 514/3, 12, 21, 514/225, 278, 319, 325; 544/380, 383, 391; 546/17, 203, 205

[56] References Cited

U.S. PATENT DOCUMENTS

| | | | |
|---|---|---|---|
| 3,239,345 | 3/1966 | Hodge et al. | 514/450 |
| 4,036,979 | 7/1977 | Asato | 514/443 |
| 4,411,890 | 10/1983 | Momany | 514/17 |
| 5,204,349 | 4/1993 | Bock et al. | 514/253 |
| 5,206,235 | 4/1993 | Fisher et al. | 514/213 |

FOREIGN PATENT DOCUMENTS

| | | |
|---|---|---|
| 0 144 230 A3 | 6/1985 | European Pat. Off. . |
| 0 486 280 A2 | 5/1992 | European Pat. Off. . |
| 0 532 097 A1 | 3/1993 | European Pat. Off. . |
| 0 533 244 A1 | 3/1993 | European Pat. Off. . |
| WO 94/13696 | 6/1994 | WIPO . |
| WO 94/19367 | 9/1994 | WIPO . |

OTHER PUBLICATIONS

R.G. Smith, et al., *Science*, Reprint Series, 11 Jun. 1993, vol. 260, pp. 1640–1643 "A Nonpeptidyl Growth Hormone Secretagogue".

*Primary Examiner*—Jeffrey E. Russel
*Attorney, Agent, or Firm*—J. Eric Thies; David L. Rose

[57] ABSTRACT

The present invention is directed to certain novel compounds identified as camphor derivatives of the general structural formula:

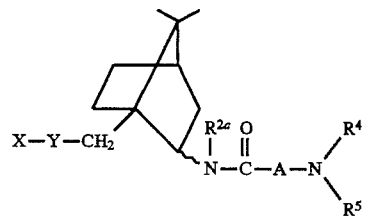

wherein A, X, Y, $R^{2a}$, $R^4$, and $R^5$ are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing such compounds as the active ingredient thereof are also disclosed.

8 Claims, No Drawings

CAMPHOR COMPOUNDS PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non-peptidal growth hormone secretagogues with a benzolactam structure are disclosed in e.g., U.S. Pat. Nos 5,206,235, 5,283,241, 5,284,841, 5,310,737 and 5,317,017. Other non-peptidal growth hormone secretagogues are disclosed in PCT Patent Pubs. WO 94/13696 and WO 94/19367. The instant compounds are low molecular weight compounds for promoting the release of growth hormone which have good stability in a variety of physiological environments and which may be administered parenterally, nasally or by the oral route. Certain camphor compounds are disclosed in EPO Patent Publications 0,486,280, 0,532,097, and 0,533,244 as being oxytocin antagonists.

SUMMARY OF THE INVENTION

The instant invention is directed to certain camphor compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the camphor compounds. It is a further object of this invention to describe procedures for the preparation of such compounds. A still further object is to describe the use of such compounds to increase the secretion of growth hormone in humans and animals. A still further object of this invention is to describe compositions containing the camphor compounds for the use of treating humans and animals so as to increase the level of growth hormone secretions. Further objects will become apparent from a reading of the following description.

DESCRIPTION OF THE INVENTION

The novel camphor compounds of the instant invention are best described in the following structural Formula I:

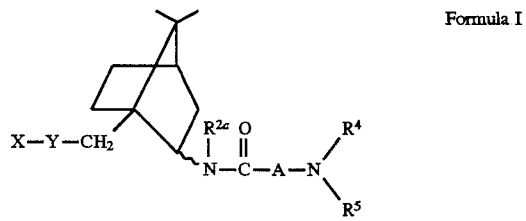

Formula I wherein:

X is selected from the group consisting of:

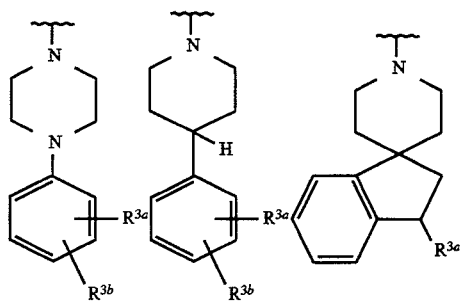

$R^{3a}$ and $R^{3b}$ are independently selected from the group consisting of: hydrogen, $C_1$–$C_6$ alkyl, halogen, —$OR^2$, —$OR^6$, —$NHSO_2CF_3$, —$(CH_2)_rOR^6$, —$(CH_2)_rN(R^2)(R^6)$, —$(CH_2)_r(R^6)$, —$(CH_2)_rC(O)OR^2$, —$(CH_2)_rC(O)OR^6$, —$(CH_2)_rOC(O)R^2$, —$(CH_2)_rOC(O)R^6$, —$(CH_2)_rC(O)R^2$, —$(CH_2)_rC(O)R^6$, —$(CH_2)_rC(O)N(R^2)(R^2)$, —$(CH_2)_rC(O)N(R^2)(R^6)$, —$(CH_2)_rN(R^2)C(O)R^2$—$(CH^2)_rN(R^2)C(O)R^6$, —$(CH_2)_rN(R^6)C(O)R^2$, —$(CH_2)_rN(R^6)C(O)R^6$, —$(CH_2)_rN(R^2)C(O)OR^2$, —$(CH_2)_rN(R^2)C(O)OR^6$, —$(CH_2)_rN(R^6)C(O)OR^2$, —$(CH_2)_rN(R^6)C(O)OR^6$, —$(CH_2)_rN(R^2)C(O)N(R^2)(R^6)$, —$(CH_2)_rN(R^2)C(O)N(R^2)(R^2)$, —$(CH_2)_rN(R^6)C(O)N(R^2)(R^6)$, —$(CH_2)_rN(R^2)SO_2R^6$, —$(CH_2)_rN(R^2)SO_2R^2$, —$(CH_2)_rN(R^6)SO_2R^2$, —$(CH_2)_rN(R^6)SO_2R^6$, —$(CH_2)_rOC(O)N(R^2)(R^6)$, —$(CH_2)_rOC(O)N(R^2)(R^2)$, —$(CH_2)_rSO_2N(R^2)(R^6)$, —$(CH_2)_rSO_2N(R^2)(R^2)$, —$(CH_2)_rSO_2NHC(O)R^6$, —$(CH_2)_rSO_2NHC(O)R^2$, —$(CH_2)_rSO_2NHC(O)OR^6$, —$(CH_2)_rSO_2NHC(O)OR^2$, —$(CH_2)_rC(O)NHC(O)N(R^2)(R^6)$, —$(CH_2)_rC(O)NHC(O)N(R^2)(R^2)$, —$(CH^2)_rC(O)NHC(O)R^6$, —$(CH_2)_rCONHC(O)R^2$, —$(CH_2)_rCONHSO_2R^6$, —$(CH_2)_rCONHSO_2R^2$, —$(CH_2)_rCONHSO_2N(R^2)(R^2)$, —$(CH_2)_rCONHSO_2N(R^2)(R^6)$, —$(CH_2)_rN(R_2)SO_2N(R^2)(R^6)$, —$(CH_2)_rN(R^6)SO_2N(R^2)(R^6)$, —$(CH_2)_rS(O)mR^6$, and —$(CH_2)_rS(O)_mR^2$;

Y is —SO$_2$— or —C(O)—;

R$^2$ is selected from: hydrogen, C$_1$–C$_6$ alkyl, and C$_3$–C$_7$ cycloalkyl, and where two C$_1$–C$_6$ alkyl groups are present on one atom, they may be optionally joined to form a C$_3$–C$_8$ cyclic ring, optionally including oxygen, sulfur or NR$^{2a}$;

R$^{2a}$ is hydrogen, or C$_1$–C$_6$ alkyl optionally substituted by hydroxyl;

R$^4$ and R$^5$ are independently hydrogen, C$_1$–C$_6$ alkyl, substituted C$_1$–C$_6$ alkyl where the substituents are 1 to 5 halo, 1 to 3 hydroxy, 1 to 3 C$_1$–C$_{10}$, alkanoyloxy, 1 to 3 C$_1$–C$_6$ alkoxy, phenyl, phenoxy, 2-furyl, C$_1$–C$_6$ alkoxycarbonyl, S(O)$_m$(C$_1$–C$_6$ alkyl); or R$^4$ and R$^5$ can be taken together to form —(CH$_2$)$_d$L$_a$(CH$_2$)$_e$— where L$_a$ is C(R$^2$)$_2$, O, S(O)$_m$ or N(R$^2$), d and e are independently 1 to 3 and R$^2$ is as defined above;

A is:

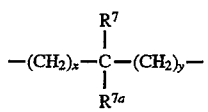

where x and y are independently 0, 1, 2 or 3;

R$^6$ is hydrogen, C$_1$–C$_6$ alkyl, or (CH$_2$)$_v$aryl, wherein the alkyl and (CH$_2$)$_v$ groups may be optionally substituted by 1–2 O(R$^2$), S(O)$_m$R$^2$, 1H-tetrazol-5-yl, C(O)OR$^2$, C(O)N(R$^2$)(R$^2$) or SO$_2$N(R$^2$)(R$^2$), N(R$^2$)C(O)N(R$^2$) (R$^2$), and where aryl is phenyl, naphthyl, pyridyl, 1H-tetrazol-5-yl, triazolyl, imidazolyl, indolyl, thiazolyl, pyrazolyl, thiadiazolyl, imidazolone-1-yl, naphthyl, oxadiazolyl, benzimidazol-2-yl, triazolinone-yl, optionally substituted with C$_1$–C$_6$ alkyl, C$_3$–C$_6$ cycloalkyl, amino, or hydroxyl;

R$^7$ and R$^{7a}$ are independently hydrogen, C$_1$–C$_6$ alkyl, trifluoromethyl, phenyl, substituted C$_1$–C$_6$ alkyl where the substituents are imidazolyl, phenyl, naphthyl, indolyl, p-hydroxyphenyl, OR$^2$, S(O)$_m$R$^2$, C(O)OR$^2$, C$_3$–C$_7$ cycloalkyl, N(R$^2$)(R$^2$), C(O)N(R$^2$)(R$^2$); or R$^7$ and R$^{7a}$ can independently be joined to one or both of R$^4$ and R$^5$ groups to form alkylene bridges between the terminal nitrogen and the alkyl portion of the R$^7$ or R$^{7a}$ groups, wherein the bridge contains 1 to 5 carbons atoms; or R$^7$ and R$^{7a}$ can be joined to one another to form a C$_3$–C$_7$ cycloalkyl;

m is 0, 1, or 2;

r is 0, 1, 2, or 3;

v is 0, 1, or 2;

and pharmaceutically acceptable salts and individual diastereomers thereof.

In the above structural formula and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl (Me), ethyl (Et), propyl (Pr), isopropyl (i-Pr), butyl (Bu), sec-butyl (s-Bu), tertiary butyl (t-Bu), pentyl, isopentyl, hexyl, isohexyl, allyl, propinyl, butadienyl, hexenyl and the like.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, propinyloxy, isobutenyloxy, hexenyloxy and the like.

The term "halogen" is intended to include the halogen atom fluorine, chlorine, bromine and iodine. The term "aryl" within the present invention, unless otherwise specified, is intended to include aromatic rings, such as carbocyclic and heterocyclic aromatic rings selected the group consisting of: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl, which may be optionally substituted by 1 to 3 of C$_1$–C$_6$ alkyl, 1 to 3 of halogen, 1 to 2 of —OR$^2$, methylenedioxy, —S(O)$_m$R$^2$, 1 to 2 of —CF$_3$, —OCF$_3$, nitro, —N(R$^2$)C(O)(R$^2$), —C(O)OR$^2$, —C(O)N(R$^2$)(R$^2$), —1H-tetrazol-5-yl, —SO$_2$N(R$^2$)(R$^2$), —N(R$^2$)SO$_2$ phenyl, or —N(R$^2$)SO$_2$R$^2$, wherein R$^2$ is as defined herein.

Certain of the above defined terms may occur more than once in the above formula or definitions and upon such occurrence, each term shall be defined independently of the other.

Preferred compounds of the instant invention include those of Formula Ia:

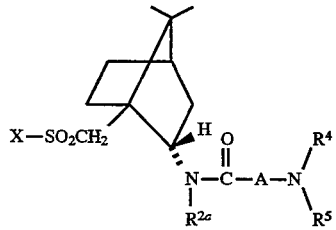

Formula Ia wherein:

X is selected from the group consisting of:

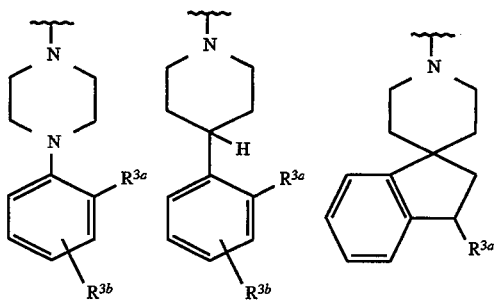

R$^{3a}$ and R$^{3b}$ are independently selected from the group consisting of: hydrogen, C$_1$–C$_6$ alkyl, halogen, —OR$^2$, —OR$^6$, —(CH$_2$)$_r$(R$^6$), —(CH$_2$)$_r$C(O)OR$^2$, —(CH$_2$)$_r$C(O)OR$^6$, —(CH$_2$)$_r$C(O)N(R$^2$)(R$^2$), —(CH$_2$)$_r$C(O)N(R$^2$)(R$^6$), —(CH$_2$)$_r$N(R$^2$)C(O)R$^2$—(CH$^2$)$_r$N(R$^2$)C(O)R$^6$, —(CH$_2$)$_r$N(R$^6$)C(O)R$^2$, —(CH$_2$)$_r$N(R$^6$)C(O)R$^6$, —(CH$_2$)$_r$N(R$^2$)C(O)OR$^2$, —(CH$_2$)$_r$N(R$^2$)C(O)N(R$^2$)(R$^6$), —(CH$_2$)$_r$N(R$^2$)C(O)N(R$^2$)(R$^2$), —(CH$_2$)$_r$N(R$^6$)C(O)N(R$^2$)(R$^6$), —(CH$_2$)$_r$S(O)$_m$R$^6$, and —(CH$_2$)$_r$S(O)$_m$R$^2$;

R$^2$ is hydrogen, C$_1$–C$_6$ alkyl, C$_3$–C$_7$ cycloalkyl and where two C$_1$–C$_6$ alkyl groups are present on one atom they may be optionally joined to form a C$_4$–C$_7$ cyclic ring optionally including oxygen, sulfur or NR$^{2a}$;

R$^{2a}$ is hydrogen or C$_1$–C$_6$ alkyl, optionally substituted by hydroxyl;

R$^4$ and R$^5$ are independently hydrogen, C$_1$–C$_6$ alkyl, or substituted C$_1$–C$_6$ alkyl where the substituents are 1 to 5 halo, 1 to 3 hydroxyl, S(O)$_m$ (C$_1$–C$_6$ alkyl) or phenyl;

$R^6$ is H, $C_1$–$C_6$ alkyl, or $(CH_2)_v$ aryl, wherein the $(CH_2)_v$ and alkyl groups may be optionally substituted by 1–2 $O(R^2)$, $S(O)_m R^2$, $C(O)OR^2$, $C(O)N(R^2)(R^2)$ or $SO_2N(R^2)(R^2)$, $N(R^2)C(O)N(R^2)(R^2)$, wherein the aryl group is selected from: phenyl, naphthyl, indolyl, pyridyl, 1H-tetrazol-5-yl, triazolyl, imidazolyl, thiazolyl, oxadiazolyl, pyrazolyl, thiadiazolyl, and benzimidazol-2-yl, which are optionally substituted with $C_1$–$C_6$ alkyl, $C_3$–$C_6$ cycloalkyl, amino, or hydroxyl;

A is:

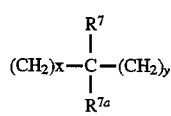

where x and y are independently 0, 1, or 2;

$R^7$ and $R^{7a}$ are independently hydrogen, $C_1$–$C_6$ alkyl, trifluoromethyl, phenyl, substituted $C_1$–$C_6$ alkyl where the substituents are imidazolyl, phenyl, naphthyl, indolyl, p-hydroxyphenyl, $OR^2$, $S(O)_m R^2$, $C(O)OR^2$, $C_5$–$C_7$ cycloalkyl, $N(R^2)(R^2)$, $C(O)N(R^2)(R^2)$; or $R^7$ and $R^{7a}$ can independently be joined to one of $R^4$ or $R^5$ to form alkylene bridges between the terminal nitrogen and the alkyl portion of $R^7$ or $R^{7a}$ groups to form 5 or 6 membered rings; or $R^7$ and $R^{7a}$ can be joined to one another to form a $C_3$ cycloalkyl;

m is 0, 1, or 2;

r is 0, 1, 2, or 3;

v is 0, 1, or 2;

and pharmaceutically acceptable salts and individual diastereomers thereof.

More preferred compounds of the instant invention include those of Formula I wherein the group:

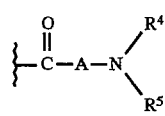

is of the formula:

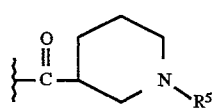

The most preferred compounds of the present invention include the following:

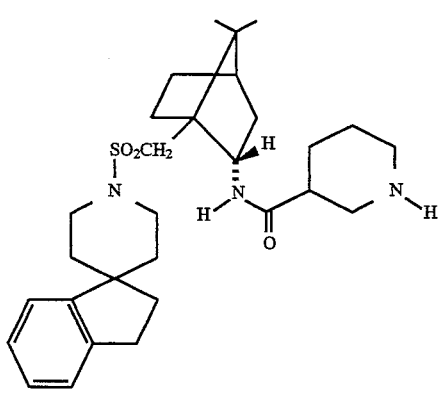

-continued

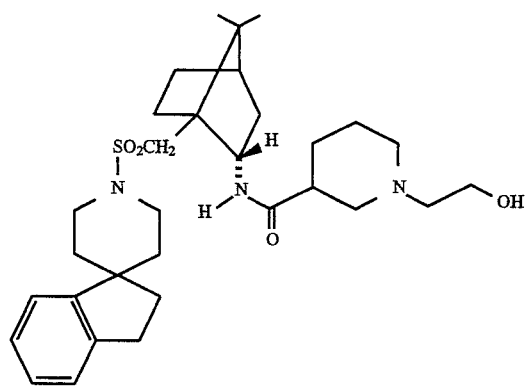

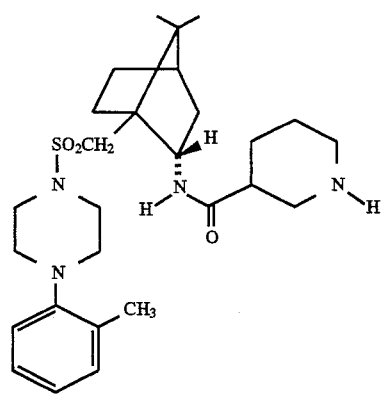

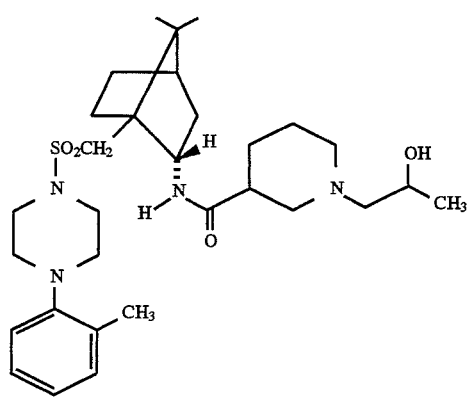

and their pharmaceutically acceptable salts and individual diastereomers thereof, where not otherwise specified.

All of the most preferred compounds shown above have asymmetric centers, which on the camphor are shown in their preferred orientation.

Throughout the instant application, the following abbreviations are used with the following meanings:

BOC t-butyloxycarbonyl
BOP Benzotriazol-1-yloxy tris(dimethylamino) phosphonium hexafluorophosphate
CBZ Benzyloxycarbonyl
DIBAL-H diisobutylaluminum hydride
DMF N,N-dimethylformamide
EDC 1-(3-dimethylaminopropyl)-3-ethylcarbodiimide hydrochloride
FAB -MS Fast atom bombardment-mass spectroscopy
GHRP Growth hormone releasing peptide
HOBT Hydroxybenztriazole
LAH Lithium aluminum hydride HPLC High pressure liquid chromatography
MHz Megahertz
MPLC Medium pressure liquid chromatography
NMM N-Methylmorpholine
NMR Nuclear Magnetic Resonance
PLC Preparative liquid chromatography
RPLC Reverse phase liquid chromatography
TFA Trifluoroacetic acid
THF Tetrahydrofuran
TLC Thin layer chromatography
TMS Tetramethylsilane The compounds of the instant invention all have asymmetric centers, including the substituted position adjacent to the bridgehead of the camphor moiety.

In addition to those present on the camphor moiety, additional asymmetric centers may be present on the molecule depending upon the nature of the various substituents on the molecule. Each such asymmetric center will produce two optical isomers and it is intended that all of the optical isomers, as separated, pure or partially purified optical isomers, racemic mixtures or diastereomeric mixtures thereof, be included within the ambit of the instant invention. Compounds which are more active as growth hormone secretagogues and, therefore are preferred, are those in which the nitrogen substituent on the camphor moiety is below and the hydrogen atom is above the plane of the structure as represented in Formula Ia:

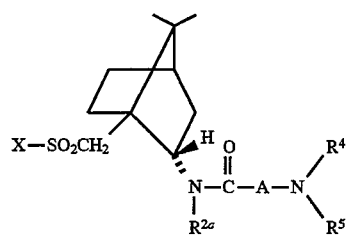

Formula Ia

Their absolute stereochemistry may be determined by X-ray crystallography of crystalline products or crystalline intermediates which are derivatized, if necessary, containing an asymmetric center of known configuration.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of the compounds of Formula I employing methodology essentially as presented in the following reaction schemes.

SCHEME 1

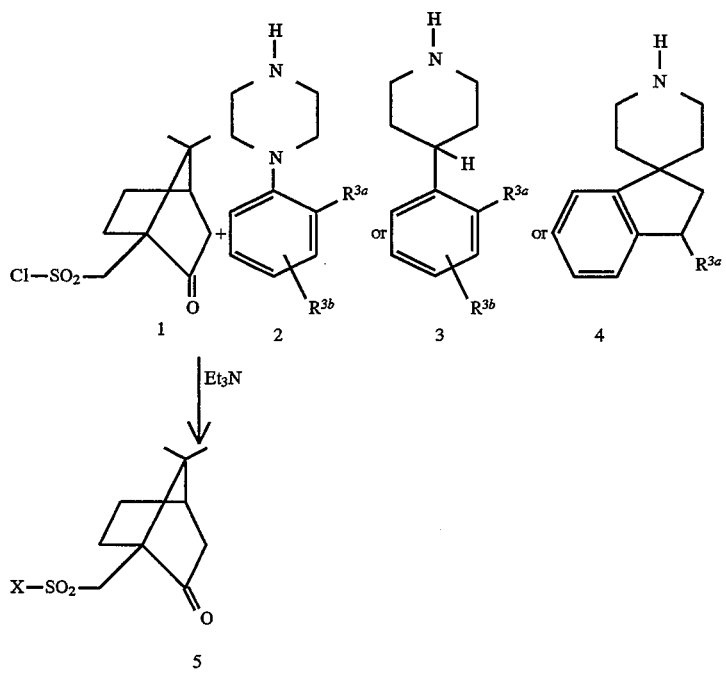

The compounds of Formula I may be prepared sequentially starting from R-camphor sulfonyl chloride. As shown in Scheme 1, reaction of R-camphor sulfonyl chloride with an intermediate 2, 3 or 4 in an inert solvent such as methylene chloride in the presence of a nonprotic organic base, such as triethylamine, gives the camphor sulfonamide 5.

SCHEME 2

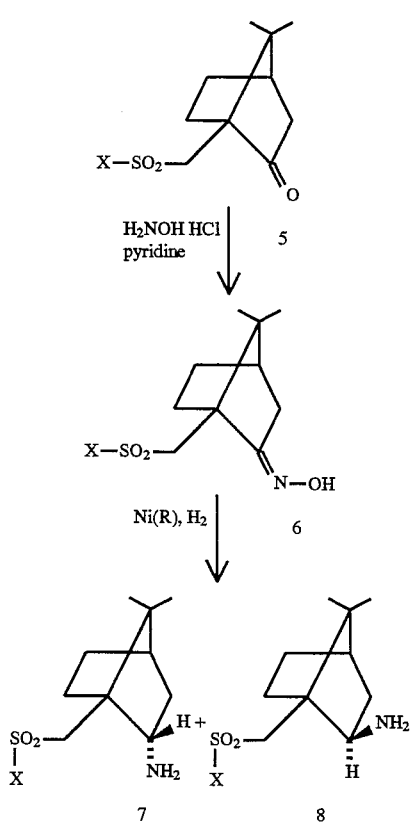

As shown in Scheme 2, the sulfonamidoketone 5 is then converted to the amino analog 7 (or 8) by methods known in the art, including via the preparation and reduction of the intermediate oxime 6. In this reduction preferred methods include catalytic reduction using RaNi. Separation of the enantiomeric amines may be achieved with flash column chromatography employing an appropriate solvent.

SCHEME 3

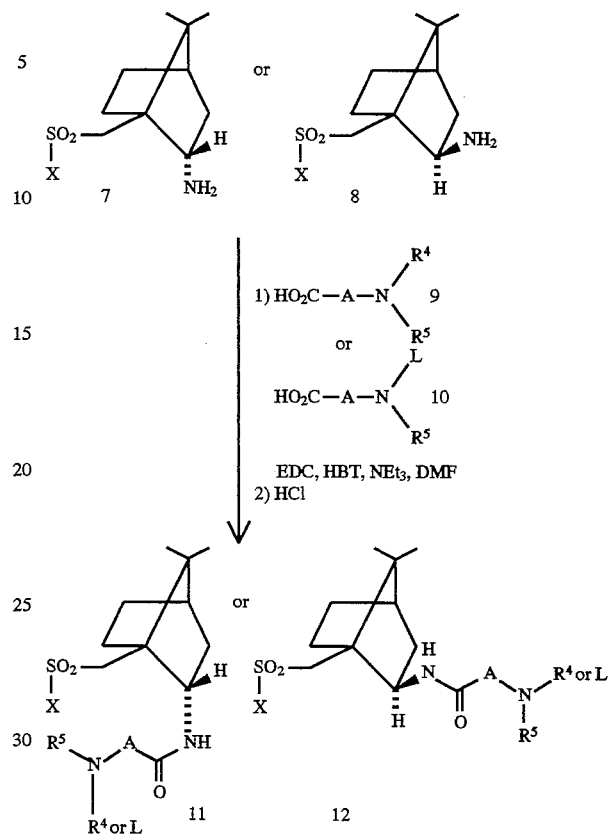

As shown in Scheme 3, the endo-amine 7 and the exo-amine 8 are readily reacted under standard peptide coupling conditions with an appropriate acid 9 or 10 (wherein the amino functionality may be protected with an appropriate protecting group L) to give the corresponding endo 11 or exo 12 derivative. The protecting group L may be removed using standard methodology and the amino groups may be further modified, for example, by reductive alkylation to afford compounds wherein $R^4$ and/or $R^5$ are other than hydrogen.

SCHEME 4

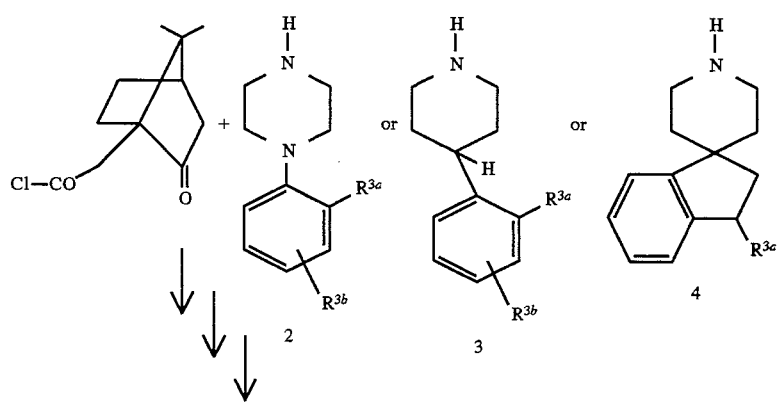

-continued
SCHEME 4

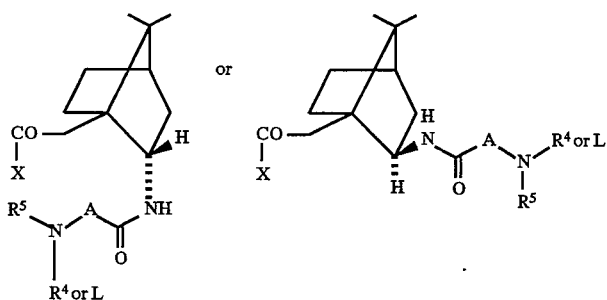

As outlined in Scheme 4, compounds of Formula I wherein Y is —C(O)— may be prepared from the appropriate camphor acyl chloride using procedures analogous to those presented in Schemes 1–3.

SCHEME 5

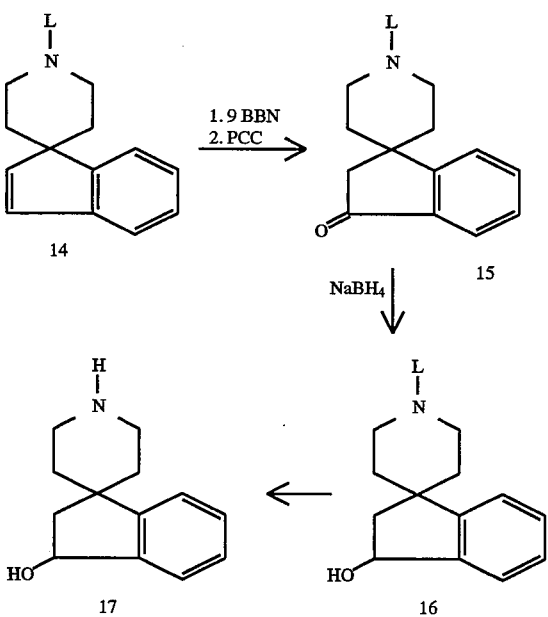

The substituted spiro-indenyl piperidines of Formula 14 are either known compounds or can be prepared by literatures procedures. Illustrated here are some, but by no means all the methods available for their preparation. The spiro-indenyl piperidine of Formula 14 wherein $R^{3a}$=H is a known compound (*J. Med. Chem.*, 35; 2033–2039 (1992)).

As shown in Scheme 5, spiroindane intermediates containing hydroxyl substituents of Formula 17, are easily prepared from the spiroindanone 15. The reduction of the ketone can be accomplished with reducing agents, for example sodium borohydride. The protecting group (L) can then be removed as noted above and the resulting hydroxyspiroindane can be employed in the chemistry described in Schemes 1–4. Alternatively the secretagogues that contain a hydroxyspiroindane functionality can be obtained from the secretagogues containing the spiroindanone by reducing the ketone as the final step in the synthesis.

Chiral hydroxy spiroindanes may be prepared by methods well known to those skilled in the art including the use of chiral reducing agents such as (S)-tetrahydro-1-methyl-3,3-diphenyl-1H,3H-pyrrolo[1,2,c][1,3,2]oxazaborole (Corey, et al., *J. Am. Chem. Soc.*, 109, 5551 (1987)). Determination of absolute stereochemistry can be achieved by a number of methods including x-ray crystallography of a suitable crystalline derivative. Derivatization with Mosher's acid may provide a suitable derivative. Alkylation and acylation of hydroxyspiroindane 16 is readily carded out with a base and the desired alkylation or acylation agent. Urethanes are formed by reacting 16 with organic isocyanates or with sodium isocyanate.

SCHEME 6

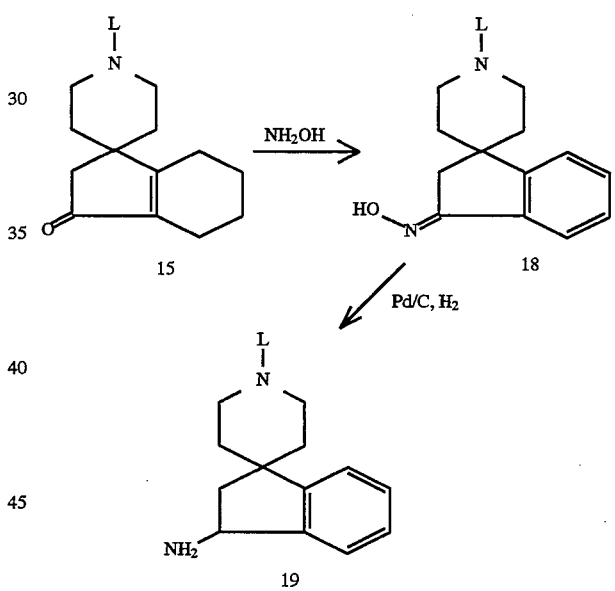

As shown in Scheme 6, the spiroindanone intermediates 15 can also serve as convenient starting materials for the incorporation of amines onto the spiroindanes. Formation of the oxime of the spiroindanone with hydroxylamine hydrochloride in a suitable solvent such as ethanol in the presence of sodium hydroxide followed by reduction of the oxime provides the amine 19. The amino group of 19 can be easily alkylated, acylated, sulfonylated or reacted with isocyanates by methods commonly known to those skilled in the art.

Chiral aminospiroindanes are available by numerous methods including resolution of the racemates by the classical methods. For example, resolution can be achieved by the formation of diastereomeric salts of the racemic amines with optically active acids such as D- and L-tartaric acid. The determination of the absolute stereochemistry can be accomplished in a number of ways including X-ray crystallography of a suitable crystalline derivative such as a D- or L-tartaric acid salt.

SCHEME 7

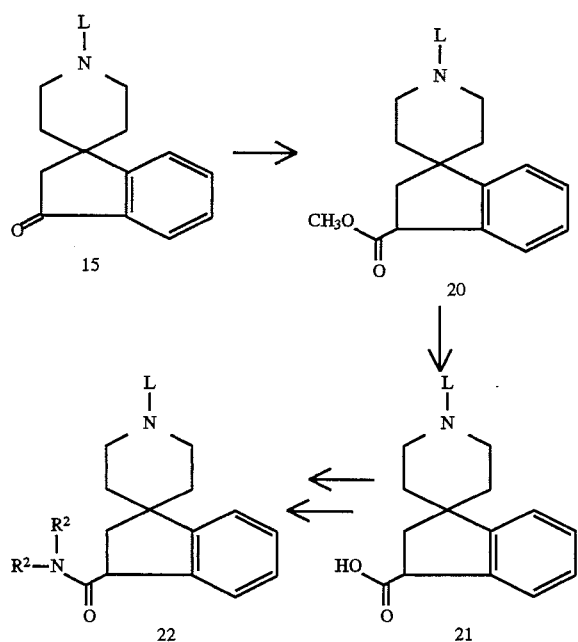

such as EDC, DCC, and BOP in an inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present are found in Greene, T; Wuts, P. G. M. *Protective Groups in Organic Synthesis*, John Wiley & Sons, Inc., New York, N.Y. (1991). CBZ and BOC were used extensively in the syntheses of this invention, and their removal conditions are known to those skilled in the art. Removal of CBZ groups can be achieved by a number of methods, for example, catalytic hydrogenation with hydrogen in the presence of palladium catalyst in a protic solvent such as ethanol. In cases where catalytic hydrogenation is contraindicated by the presence of other potentially reactive functionality removal of CBZ groups can also be achieved by treatment with a solution of hydrogen bromide in acetic acid, or by treatment with a mixture of TFA and dimethylsulfide. Removal of BOC protecting groups is carded out in a solvent such as methylene chloride or methanol, with a strong acid, such as trifluoroacetic acid (TFA) or hydrochloric acid (HCl).

The substituted piperidines of Formula 3 are either known compounds or can be prepared by literature procedures. Illustrated here are some, but by no means all the methods available for their preparation.

SCHEME 8

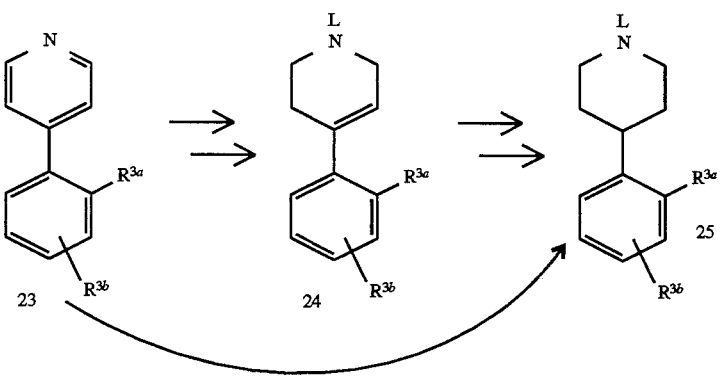

As shown in Scheme 7, chiral carboxy-substituted spiroindanyl piperidines of Formula 21 may be prepared by a carbonylation reaction of the enol triflate derived from the ketone 15 in the presence of a palladium(O) catalyst in methanol. The protecting group L of 20 may be removed and elaborated to ester bearing camphor compounds by using chemistry shown in Schemes 1–4.

The ester of 20 can hydrolyzed to the acid 21 by a variety of methods that are familiar to those skilled in the art. Chiral carboxyl spiroindanes can be prepared by methods familiar to those skilled in the art including resolution of diastereomeric salts of racemic acid with optically active amines. The acid 21 can be converted to carboxamides of Formula 22 by carrying out a peptide-type coupling reaction with amines of formula HN(R²)(R²). The protecting group L of 22 can be removed and elaborated to the instant compounds by using chemistry detailed in Schemes 1–4.

The phrase "standard peptide coupling reaction conditions" is used repeatedly here, and it means coupling a carboxylic acid with an amine using an acid activating agent The synthesis of substituted piperidines of Formula 3 has been detailed in a number of research articles. For e.g., S. M. N. Efange et al., (*J. Med. Chem.*, 36, 1278–1283 (1993)) and M. S. Berridge et al., (*J. Med. Chem.*, 36, 1284–1290 (1993)) have used 4-substituted-pyridine intermediates 23 to synthesize 4-substituted tetrahydropiperidines of Formula 24 (L=methyl) as detailed in Scheme 8. Removal of L from piperidines of Formula 24 can be carded out by a number of methods familiar to those skilled in the art, including the cyanogen bromide protocol detailed by H. Ong et al., in *J. Med. Chem.*, 23,981–986 (1983) and ACE-Cl method as described in R. Olofson et al., *J. Org. Chem.*, 23, 2795 (1984). For intermediates of Formula 24, wherein L=Bn, simultaneous removal of the benzyl group and hydrogenation of the olefin can be accomplished by use of platinum or palladium catalysts in a protic solvent like methanol. Alternatively, 23 can be directly transformed to piperidines of Formula 25 (L=H) by carrying out the reduction with platinum oxide in a protic solvent such as methanol with a catalytic amount of acid.

SCHEME 9

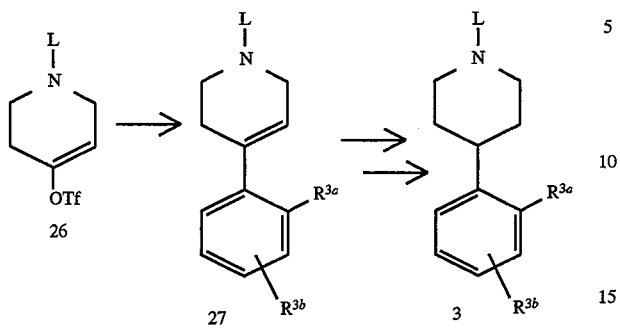

As shown in Scheme 9, other methods may also be used to synthesize compounds of Formula 3. For example, cross-coupling of enol triflates of Formula 26 (L=protecting group) with phenyl boronic acid or phenyl tin reagents can be accomplished with palladium (II) or palladium (O) catalysts as detailed in the review article by W. J. Scott and J. E. McMurry *Acc. Chem. Res.*, 21, 47 (1988) to give tetrahydropiperidines 27 (L=protecting group). Various methods exist for the synthesis of the enol triflate intermediates of Formula 26, phenyl boronic acids, and phenyl tin compounds that are familiar to those skilled in the art. Hydrogenation of 27 followed by removal of the protection group L also gives saturated derivatives 3 that may be elaborated to compounds of Formula I.

SCHEME 10

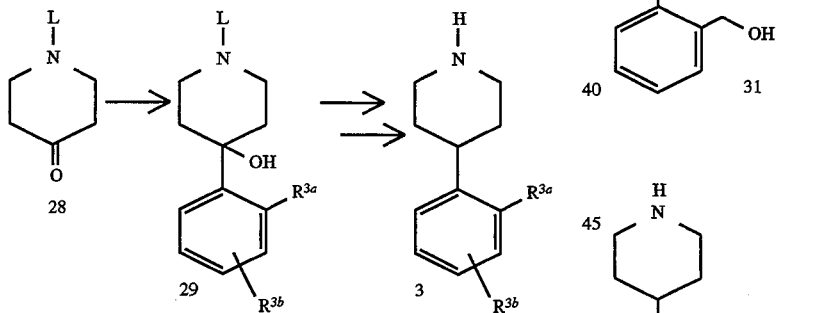

As shown in Scheme 10, other methods for the synthesis of substituted piperidines also involve addition of substituted and/or unsubstituted phenyl. Grignard reagents or lithium reagents may be added to oxo-piperidines of Formula 28 (L=benzyl, methyl, etc.) to give compounds of Formula 29 (L=benzyl, methyl, etc.). The dehydration of the hydroxyl group of 29 (L=benzyl, methyl, etc.) may be carried out by treating it with strong acid or via an elimination reaction of the corresponding mesylate derived from 29 (L=benzyl, methyl, etc.) and the olefin compound may be transformed to 3 as described above.

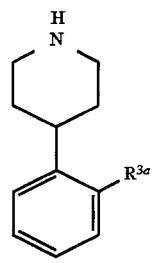

Specifically, ortho-substituted phenyl piperidines of Formula 30 can be prepared from the phenyl piperidine intermediate 31 (see S. M. N. Efange et al., *J. Med. Chem.*, 26, 1278 (1993)).

SCHEME 11

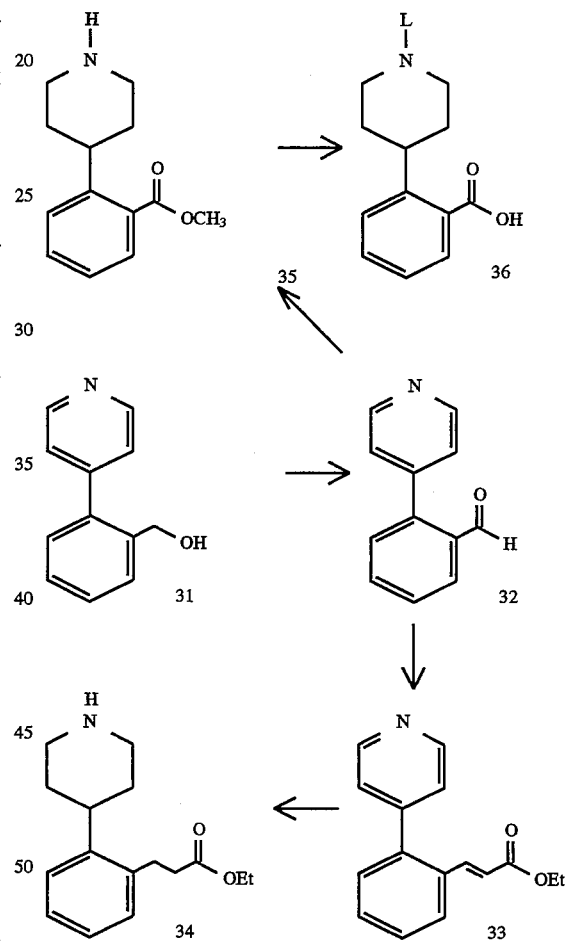

As shown in Scheme 11, the benzyl alcohol can be oxidized to aldehyde 32 by a variety of methods familiar to those skilled in the art. Commonly used methods are manganese dioxide in an inert solvent like chloroform or the Swern protocol. A variety of functional groups can now be elaborated from 32. For example, an Emmons reaction with triethylphosphonoacetate in the presence of base gives the α,β-unsaturated ester 33. Concurrent reduction of the pyridine unit and the olefin group with a platinum or palladium catalyst in an alcoholic solvent provides the piperidine of Formula 34. The piperidine 34 may be derivatized to ester and acid bearing compounds of Formula I by using chemistry detailed in Schemes 1–4. Alternatively, 32 can directly be transformed to a methyl ester 35, by oxidation of the aldehyde group to an ester with the Corey protocol (NaCN, acetic acid, $MnO_2$, in methanol) followed by reduction of the pyridine to a piperidine with platinum or palladium catalysts in a protic solvent like methanol. The piperidine 35 can be elaborated to compounds of Formula I by using chemistry detailed in Schemes 1–4. The piperidine unit of 35 can be protected by a variety of protecting groups L familiar to those skilled in the art and the ester unit can be hydrolyzed by well documented methods to give the acid 36. The acid intermediate 36 can be used to prepare compounds bearing a variety of highly functionalized piperidines that can be transformed to the compounds of Formula I.

Highly functionalized phenyl piperidines of Formula 30 may also be prepared by utilizing synthetic methods detailed below.

SCHEME 12

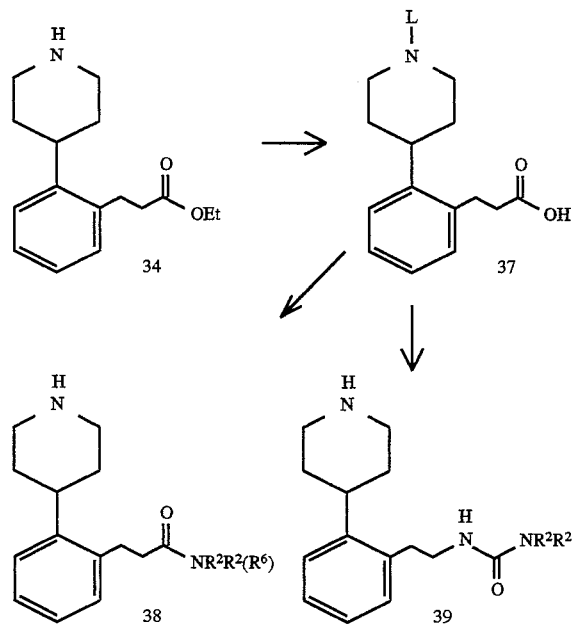

As depicted in Scheme 12 the piperidine 34 may also serve as a key intermediate for the synthesis of a variety of piperidines of Formula 30, wherein $R^{3a}$ is an alkyl and aryl amide, alkyl and aryl acylsulfonamide, alkyl and aryl urea, alkyl and aryl carbamate, etc. The piperidine nitrogen of 34 can be protected with a protecting group L (appropriate groups include BOC, CBZ, FMOC) by well documented methods and the ester unit may be hydrolyzed with sodium or potassium hydroxide in aqueous or alcoholic media to give 37. Peptide type coupling of 37 with primary and secondary aliphatic mines, aryl amines, suitably protected amino acids, alkyl or aryl sulfonamides provides amides of Formula 38 after removal of the protecting group L. Alternatively, the acid 37 can be activated with carbonyl diimidazole and subsequently reacted with primary and secondary aliphatic amines, aryl amines, suitably protected amino acids, alkyl or aryl sulfonamides in an inert solvent like tetrahydrofuran or dimethylformamide to give amides of Formula 38 wherein $R^2$ may be any of the groups within the scope of this invention. The ureas of Formula 39 may be synthesized from 37 by carrying out a Curtius rearrangement and trapping the isocyanate intermediate with amines of formula $HNR^2R^2$. The protecting group L can be removed and elaborated to compounds of Formula I using chemistry presented in Schemes 1–4.

SCHEME 13

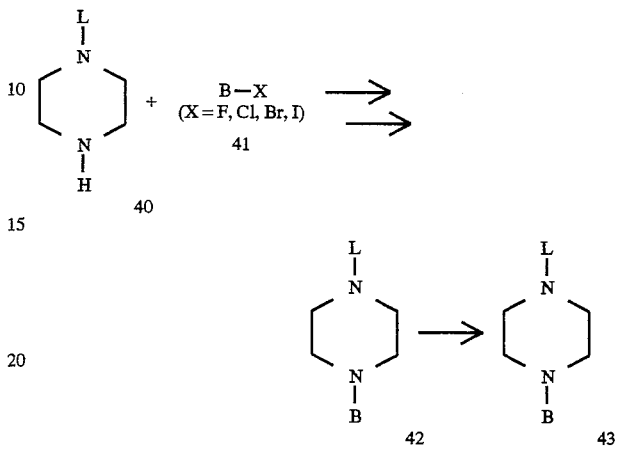

The synthesis of substituted phenyl piperazines of Formula 2 has been detailed in a number of research articles. One of the standard approaches to the synthesis of aryl piperazines involves a nucleophilic aromatic substitution reaction as shown in Scheme 13. The reaction of a protected piperazine of Formula 40 (L=BOC, CBZ, etc.) with a halo-aromatic reactant of Formula 41 (B—X; wherein X=Cl, F, Br, or I; usually F) in the presence of a base and/or Cu gives substituted piperazines 42 (L=BOC, CBZ, etc.). Removal of the protecting group L can be accomplished by methods familiar to those skilled in the art. These deblocked piperazines can be elaborated to the compounds of Formula I using chemistry detailed in Schemes 1–4.

SCHEME 14

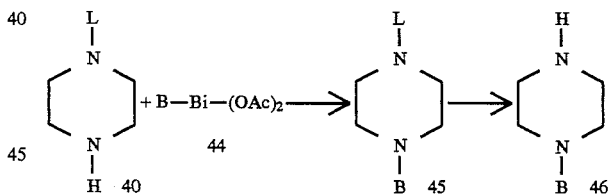

Other methods that may be employed to prepare phenyl piperazines include the copper catalyzed N-arylation of amines by triarylbismuth diacetates (D. H. R. Barton, et al., Tetrahedron Lett., 27, 3615–3618 (1986)) as shown in Scheme 14.

SCHEME 15

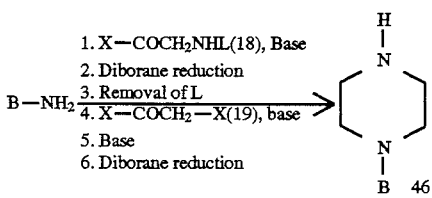

Another method that may be employed to synthesize phenyl piperazines involves the elaboration of the piperazine unit from anilines via a multistep sequence as shown in Scheme 15.

SCHEME 16

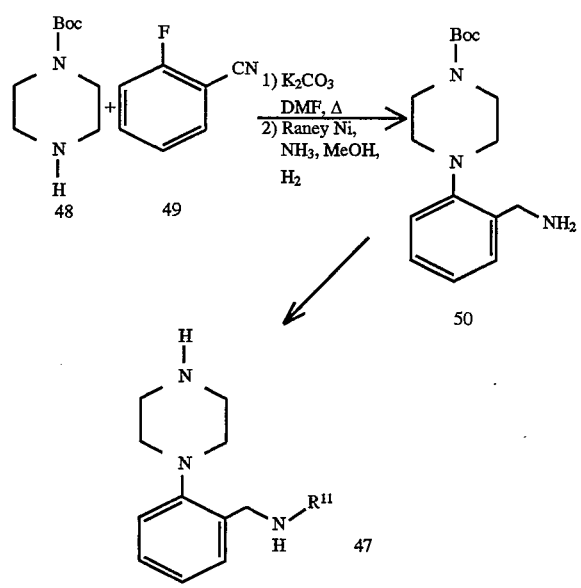

The synthesis of functionalized phenyl-piperazines of Formula 47 may be carded out as shown as shown in Scheme 16. Addition of the commercially available piperazine 48 to o-fluoro-benzonitrile 49 proceeds well in the presence of potassium carbonate in DMF. Reduction of nitrile to amine 50 can be carried out by hydrogenation with Raney nickel in methanolic ammonia. The phenyl piperazine intermediate 50 can be derivatized in a variety way to obtained highly functionalized intermediates of Formula 47. Reaction of the amino unit of 50 with sulfonyl chlorides provides sulfonamides, isocyanides yields ureas, acid chlorides or acid anhydrides gives amides, sulfamoyl chlorides gives sulfamides, chloroformates gives carbamates and so on and so forth. Removal of the BOC protecting group with acid gives the functionalized intermediate 47 that can be elaborated to the present compounds using the chemistry detailed in Schemes 1–4.

SCHEME 17

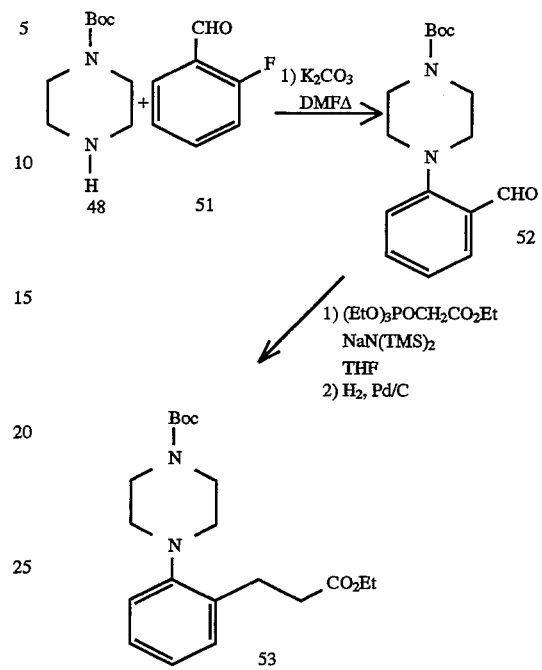

The synthesis of functionalized phenyl-piperazines of Formula 53 can be carded out as shown in Scheme 17. Addition of the commercially available piperazine 48 to o-fluoro-benzaldehyde 51 proceeds well in the presence of potassium carbonate in DMF. The phenyl piperazine intermediate 52 can be derivatized in a variety ways to obtained highly functionalized intermediates. A Horner-Emmons condensation of 52 with triethylphosphonoacetate and hydrogenation of the α,β-ester intermediate provides 53. Removal of the BOC group of 53 and elaboration to ester bearing compounds may be carded out by using chemistry detailed in Scheme 1–4.

SCHEME 18

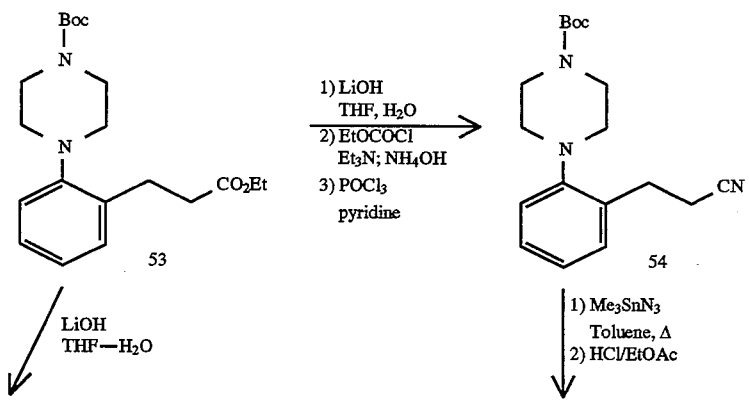

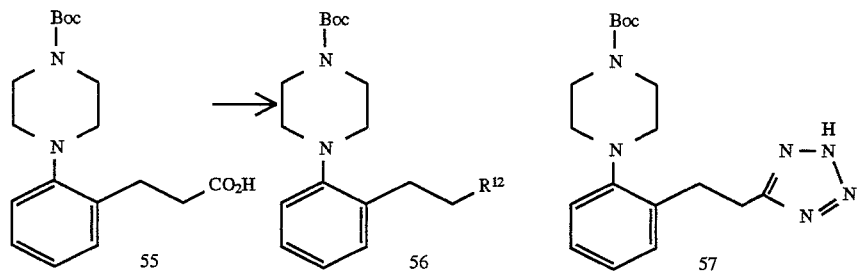

As shown in Scheme 18 the ester unit of 53 may be transformed to the nitrile 54 in a straightforward manner. Reaction of 54 with trimethyltin azide in refluxing toluene provides the tetrazole 57 after removal the BOC protecting group. As shown previously, elaboration of 57 to the tetrazole bearing secretagogues can be carried out by using chemistry detailed in Schemes 1–4 after removal of the protecting group. Other functionalized phenyl piperazines of Formula 56 wherein $R^{12}$ is a urea or an amide group are accessed from the intermediate 53 as shown in Scheme 8.

It is noted that in some situations the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay described by Smith, et al., Science, 260, 1640–1643 (1993) (see text of FIG. 2 therein). In particular, the intrinsic growth hormone secretagogue activities of the compounds of the present invention may be demonstrated in this assay. The compounds of the following examples have activity in the aforementioned assay in the range of 1 μnM to 5 μM.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release and that the growth hormone releasing factor (GRF) stimulates its release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to, TRH, diethylstilbesterol, estrogens, β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the growth hormone secretagogues of this invention is in combination with other growth hormone secretagogues such as the growth hormone releasing peptides GHRP-6, GHRP-1 as described in U.S. Pat. Nos. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. For example, a compound of the present invention may be used in combination with IGF-1 for the treatment or prevention of obesity. In addition, a compound of this invention may be employed in conjunction with retinoic acid to improve the condition of musculature and skin that results from intrinsic aging.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses may be summarized as follows: treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia, treatment of peripheral neuropathies; replacement of growth hormone in stressed patients; treatment of osteochondrody-splasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and prevention of the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in musculature, muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock. Likewise, the instant compounds are useful in a method of treatment of diseases or conditions which are benefited by the anabolic effects of enhanced growth hormone levels that comprises the administration of an instant compound.

In particular, the instant compounds are useful in the prevention or treatment of a condition selected from the group consisting of: osteoporosis; catabolic illness; immune deficiency, including that in individuals with a depressed $T_4/T_8$ cell ratio; hip fracture; musculoskeletal impairment in the elderly; growth hormone deficiency in adults or in children; obesity; cachexia and protein loss due to chronic illness such as AIDS or cancer; and treating patients recovering from major surgery, wounds or burns, in a patient in need thereof.

In addition, the instant compounds may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drag addiction, and fertility problems.

It will be known to those skilled in the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T., "Role of Bisphosphonates in Metabolic Bone Diseases" *Trends in Endocrinol. Metab.*, 4, 19–25 (1993). Bisphosphonates with these utilities include alendronate, tiludronate, dimethyl-APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate.

Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg. of body weight daily are administered to patients and animals, e.g., mammals, to obtain effective release of growth hormone.

The following examples are provided for the purpose of further illustration only and are not intended to be limitations on the disclosed invention.

EXAMPLE 1

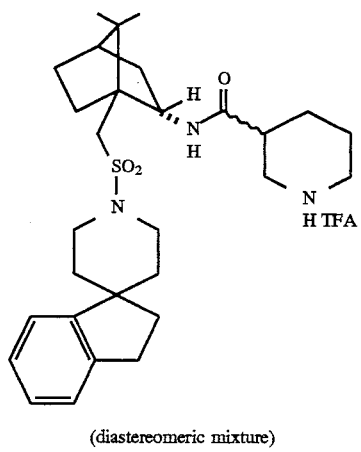

(diastereomeric mixture)

Step 1:

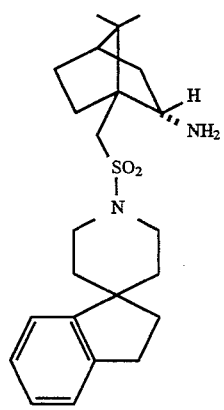

This endo-amine intermediate was prepared from (+)-camphorsulfonylchloride and spiro [1H-indene, -1,4'-piperidine] as described in European Pat. Application EP 0,533,244.

Step 2:

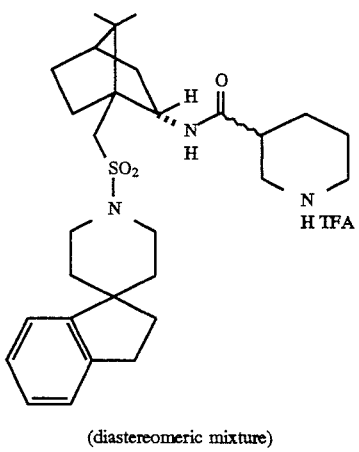

(diastereomeric mixture)

To a solution of 13 mg of the amine intermediate from Step 1 and 12 mg of (RS)-N-tBOC nipecotic acid in 2.0 mL of chloroform was added 24 mg of EDC and stirred at room temperature for 3 h. The reaction mixture was diluted with 10 mL of chloroform and washed with 5 mL of 1N HCl solution, 5 mL of saturated NaHCO$_3$ solution, dried over MgSO$_4$ and concentrated. The residue was purified by flash chromatography (2 g silica gel) with CHCl$_3$—MeOH (25:1) as the eluent to give 7.4 mg of the coupled product. This material was treated with 1 mL of TFA and 0.10 mL of anisole for 30 min. The reaction mixture was concentrated, toluene was added to the residue and evaporated to dryness. The residue was triturated with ether to give the tide compound.

$^1$H NMR (CD$_3$OD; 400 MHz) 8.15 and 8.02 (2 doublets, 1H), 7.25–7.05 (m, 4H), 4.52–4.38 (m, 1H), 3.80–3.60 (m, 2H), 3.50–2.90 (m, 9H), 2.90–2.73 (m, 1H), 2.37 (q, 1H), 2.20–1.60 (m, 16H), 1.40 (m, 1H), 1.08 (s, 3H), 1.00 (s, 3H).

EXAMPLE 2

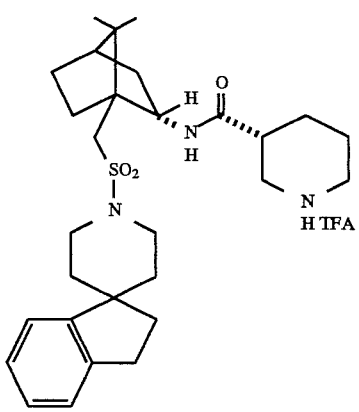

The title compound was prepared as described in Example 1 but (R)-N-tBOC nipecotic acid was used in place of (RS)-N-tBOC nipecotic acid.

$^1$H NMR (CDCl$_3$; 400 MHz) 9.80 (bs, 1H), 8.60 (bs, 1H), 7.30–7.05 (m, 4H), 4.35 (bs, 1H), 3.80–3.60 (m, 2H), 3.55–2.70 (m, 9H), 2.40 (m, 1H), 2.30–1.70 (m, 17H), 1.35 (m, 1H), 1.01 (s, 3H), 0.92 (s, 3H).

EXAMPLE 3

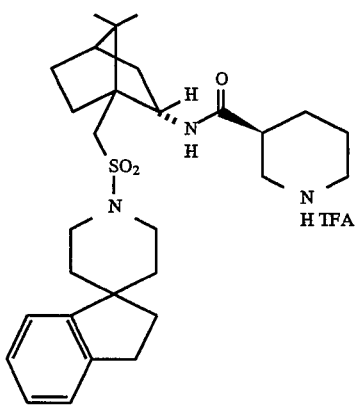

The 2 diastereomers that are generated by coupling the amine intermediate synthesized in Step 1 of Example 1 with (RS)-N-tBOC nipecotic acid were separated by prep TLC with chloroform-ether (25:1) as the eluent. The two compounds were deprotected separately by the TFA protocol as described above. The $^1$H NMR of the more polar diastereomer obtained after chromatography matched very well with the compound synthesized in Example 2. Hence, stereochemistry of the nipecotic acid side chain of the less polar diastereomer (title compound) was assigned to be (S).

$^1$H NMR (CDCl$_3$; 400 MHz) 9.80 (bs, 1H), 8.70 (bs, 1H), 7.30–7.05 (m, 4H), 6.85 (bs, 1H), 4.25 (bs, 1H), 3.80–3.60 (m, 2H), 3.55–2.80 (m, 9H), 2.40 (m, 1H), 2.20–1.60 (m, 17H), 1.35 (m, 1H), 1.03 (s, 3H), 0.95 (s, 3H).

EXAMPLES 4–8

The compounds in Table 1 were prepared as described in Step 2 of Example 1 but other N-tBOC amino acids were used in place of (RS)-N-tBOC nipecotic acid.

TABLE 1

| Example # | R | Characteristic $^1$H NMR peaks |
|---|---|---|
| 4 | ⟨C(=O)C(CH₃)₂NH₂·TFA⟩ | 8.55 (bs, 2H), 7.20–7.05 (m, 4H), 1.70 (s, 3H), 1.63 (s, 3H), 1.00 (s, 3H), 0.91 (s, 3H). |
| 5 | ⟨C(=O)CH₂C(CH₃)₂NH₂·TFA⟩ | 830 (bs, 2H), 7.25–7.10 (m, 4H), 1.48 (s, 3H), 1.36 (s, 3H), 0.97 (s, 3H), 0.92 (s, 3H). |
| 6 | ⟨C(=O)-piperidine·HTFA⟩ | 8.28 and 8.21 (2d, 1H), 3.80–3.70 (m, 3H) 1.12 and 1.10 (2s, 3H), 1.06 and 1.05 (2s, 3H). |
| 7 | ⟨C(=O)CH(CH₂CH₂NHTFA)CH₂CH₃⟩ | 9.50 (bs, 1H), 8.70 (bs, 1H), 3.50–3.40 (m, 2H), 0.98 (s, 3H), 0.94 (s, 3H). |
| 8 | ⟨C(=O)CH(NH)-pyrrolidine⟩ | 6.58 and 6.55 (2d, 1H), 4.20 and 4.14 (2q, 1H), 3.40–3.38 (m, 1H), 0.97 (s, 3H), 0.94 and 0.92 (2s, 3H). |

EXAMPLE 9

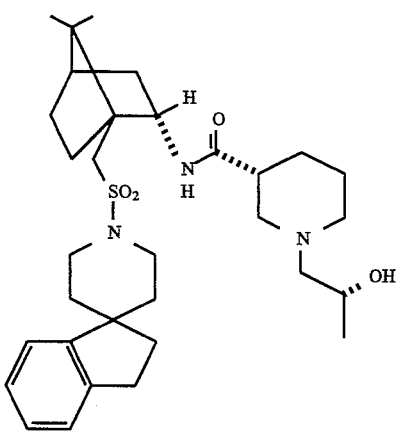

A mixture of 6.5 mg of the compound prepared in Example 2, 0.010 mL of triethylamine, and 0.10 g of neutral alumina and 0.20 mL of (S)-propylene oxide were stirred in tightly capped vial for 16 h. The alumina filtered off through a pad of celite and the filtrate was concentrated. The residue was diluted with 10 mL of chloroform and washed with saturated $Na_2CO_3$ solution (2×5 mL), dried over $K_2CO_3$, and concentrated. The residue was purified by prep TLC (0.50 mm plate) with chloroform-methanol (10:1) as the eluent to give 4.5 mg of the title compound as a colorless oil.

$^1$H NMR ($CD_3OD$; 400 MHz) 7.25–7.12 (m, 4H), 6.95 (bs, 1H), 4.23 (q, 1H), 4.12–3.85 (m, 1H), 3.81–3.65 (m, 2H), 3.15–2.85 (m, 7H), 2.70–2.50 (m, 1H), 2.50–2.30 (m, 3H), 2.71–1.49 (m, 17H), 1.40–1.20 (m, 1H), 1.16 and 1.15 (2d, 3H), 0.98 (s, 3H), 0.95 (s, 3H).

EXAMPLE 10

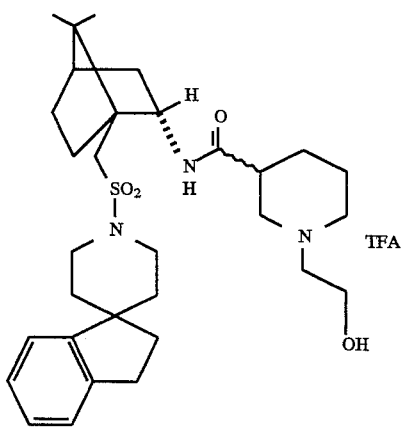

To a solution of 41 mg of the compound prepared in Example 1 in dry 9DMF was added 45 g of powdered potassium carbonate, and 18 mg of 2-t-butyldimethylsilyloxy-1-bromoethane and heated at 50° C. for 18 h. The reaction mixture was diluted with 10 mL of water and extracted with chloroform (3×10 mL). The combined organics were washed with brine (10 mL), dried over $MgSO_4$ and concentrated to give a thick oil. This material was purified by flash chromatography (5 g silica gel) with chloroform-methanol (25:1) as the eluent to 16.4 mg of the tertiary amine product as a 2:1 mixture of compounds. This material was stirred in 1 mL of TFA, 1.0 mL of THF and 0.20 mL of water at room temperature. The reaction was warmed at 45° C. for 1 h and then the volatiles were removed and the residue was diluted with toluene and evaporated to dryness. The residue was triturated with ether and the solvent was decanted. The title compound was obtained as a colorless solid.

$^1$H NMR ($CDCl_3$; 400 MHz) 7.25–7.10 (m, 4H), 6.79 (d, 1H), 4.23 (q, 1H), 4.40–4.23 (m, 1H), 4.05–3.90 (m, 2H), 3.80–3.60 (m, 4H, 3.35–2.76 (m, 10H), 2.65 (m, 1H), 2.40 (9, 1H), 2.30–1.55 (m, 17H), 1.40–1.30 (m, 1H), 0.97 (s, 3H), 0.95 and 0.93 (s,3H).

EXAMPLE 11

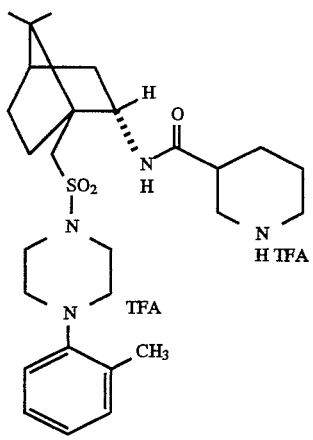

Step 1:

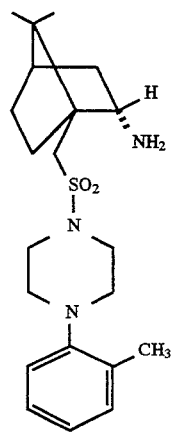

This endo-amine intermediate was synthesized from (+)-camphorsulfonyl chloride and o-tolylpiperazine as described in European Pat. Application EP 0.532,097.

Step 2:

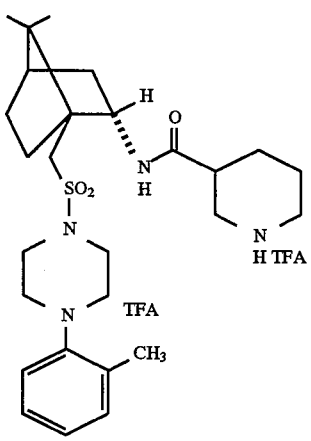

The endo-amine from Step 1 was coupled with (RS)-N-tBOC nipecotic acid as described in Step 2 of Example 1. The two diastereomers were separated by prep TLC with chloroform-ether (25:1) as the eluent. The more polar diastereomer was deblocked by the TFA/anisole protocol as described above to give the title compound as a pale yellow solid.

$^1$H NMR (CDCl$_3$; 400 MHz) 8.30 (bs, 1H), 7.20–7.10 (m, 2H), 7.05–6.90 (m, 2H), 4.30 (bs, 1H), 3.50–3.10 (m, 10H), 2.98 (bs, 4H), 2.90–2.70 (m, 2H), 2.40 (m, 1H), 2.28 (s, 3H), 2.10–1.40 (m, 10H), 1.34 (m, 1H), 0.98 (s, 3H), 0.91 (s, 3H).

EXAMPLE 12

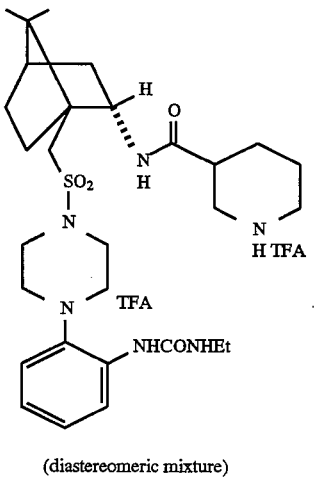

(diastereomeric mixture)

Step 1:

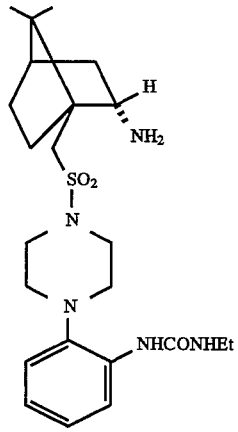

To a solution of 2.09 g of 2-nitrophenyl piperazine trifluoroacetate in 20 mL of CH$_2$Cl$_2$ and 2.40 mL of triethylamine at room temperature was added 1.75 g of (+)-camphorsulfonyl chloride and stirred for 1 h. The reaction mixture was poured into 50 mL of EtOAc and washed with 2×10 mL of aqueous citric acid, 10 mL of saturated NaHCO$_3$ solution, dried over K$_2$CO$_3$ and concentrated to yield 3.67 g of the sulfonamide that was used without purification.

To a solution of 3.67 g of the above intermediate in 25 mL of ethanol and 5 mL of dioxane was added 1.0 g of ethanol washed Raney nickel and hydrogenated for 3 h. The catalyst was filtered through celite and the filtrate was concentrated to 3.47 g of the aniline as a colorless solid.

The above intermediate was reacted with 3 mL of ethylisocyanate in 20 mL of CH$_2$Cl$_2$ for 12 h. The reaction mixture was concentrated and solid residue was rinsed with ether and dried to give 1.58 g of the urea that was used without purification.

To a solution of 1.58 g of the urea in 10 mL of pyridine was added 1.29 g of hydroxylamine hydrochloride and stirred for 12 days. The volatiles were removed on the rotary evaporator and the residue was taken up in 50 mL of water and extracted with EtOAc (3×50 mL). The combined organics were washed with water, brine, dried over Na$_2$SO$_4$ and concentrated to give the oxime as a colorless foam.

To a suspension of 0.70 g of the oxime and 2.0 g of nickel/aluminum alloy in 10 mL of ethanol was added 2.0 mL of 50% aqueous NaOH and once the exotherm has subsided the reaction mixture was refluxed overnight. The solids were filtered off and washed with chloroform. The organic layer was separated, dried over K$_2$CO$_3$ and concentrated. Flash chromatography of the residue with chloroform-methanol (10:1) as the eluent gave 66 mg of the less polar exo-amine and 0.129 g of the endo-amine.

$^1$H NMR (CDCl$_3$; 400 MHz) of the endo-amine: 7.88 (d, 1H), 7.05–6.92 (m, 3H), 6.83 (t, 1H), 3.40–3.25 (m, 5H), 3.12 (q, 2H), 2.90–2.73 (m, 6H 2.30–2.20 (m, 1H), 1.97 (dt, 1H), 1.74 (dt, 1H), 1.64–1.50 (m, 2H), 1.18 (dt, 1H), 1.02 (t, 3H), 0.86 (s, 3H), 0.84 (s, 3H), 0.71 (dd, 1H).

Step 2:

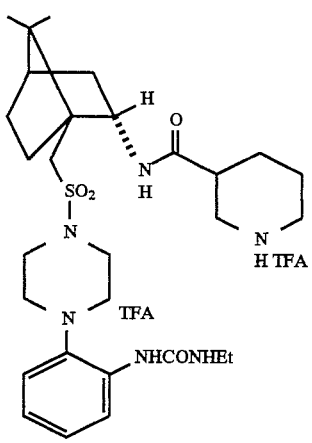

(diastereomeric mixture)

The title compound was prepared by a two-step sequence from the endo-amine intermediate prepared in Step 1 and (RS) N-tBOC-nipecotic acid as described in Example 1.

$^1$H NMR (CDCl$_3$; 400 MHz) 8.20 (d, 1H), 8.10 (d, 1H), 7.94 (d, 1H), 7.18 (t, 1H), 7.03 (t, 1H), 6.97 (t, 1H), 4.51–4.37 (m, 1H), 3.54–2.70 (m, 15H), 2.48–2.30 (m, 1H), 2.20–1.55 (m, 10H), 1.42 (bs, 1H), 1.15 (t, 3H), 1.05 (s, 3H), 1.00 and 0.98 (2s, 3H).

EXAMPLE 13

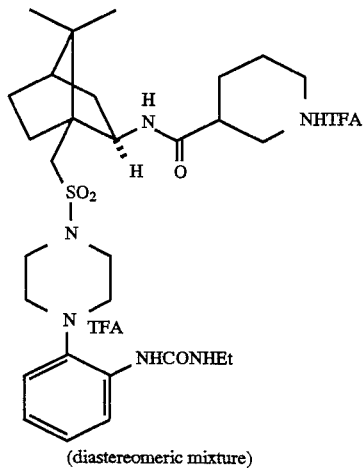

(diastereomeric mixture)

Step 1:

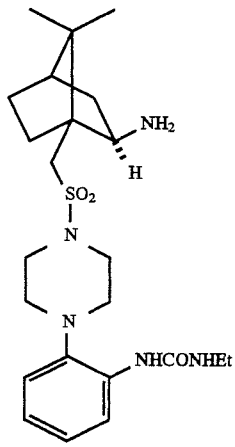

The synthesis of the exo-amine has been described in Step 1 of Example 12.

$^1$H NMR (CDCl$_3$; 400 MHz) 7.90 (d, 1H), 7.15–7.05 (m, 3H), 6.98 (dd, 1H), 5.02 (bs, 1H), 3.50–3.28 (m, 7H), 2.96–2.86 (m, 4H), 1.69 (d, 1H), 1.90–1.63 (m, 6H), 1.50 (m, 1H), 1.20 (t, 3H), 1.04 (s, 3H), 0.81 (s, 3H).

Step 2:

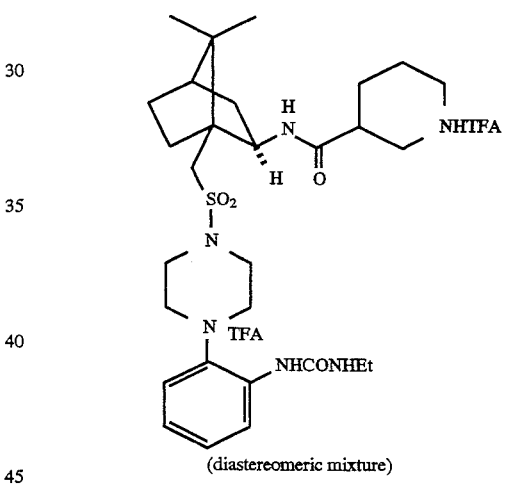

(diastereomeric mixture)

Prepared from the intermediate synthesized above by using chemistry described in Example 12.

$^1$H NMR (CDCl$_3$; 400 MHz) 7.92 (dd, 1H), 7.80 (d, 1H), 7.19 (d, 1H), 7.05 (t, 1H), 6.95 (t, 1H), 4.10 (m, 1H), 3.60–2.70 (m, 16H), 2.20–1.40 (m, 10H), 1.30 (bs, 1H), 1.18 (t, 3H), 1.05 (s, 3H), 0.98 (s, 3H).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A composition useful for increasing the endogenous production or release of growth hormone in a human or an animal which comprises an inert carrier, an effective amount of a compound of the Formula I:

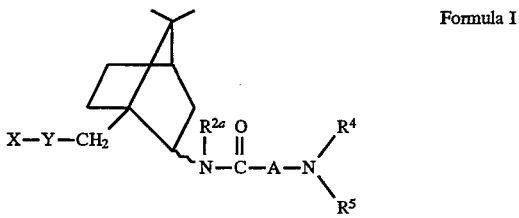

Formula I wherein:

X is selected from the group consisting of:

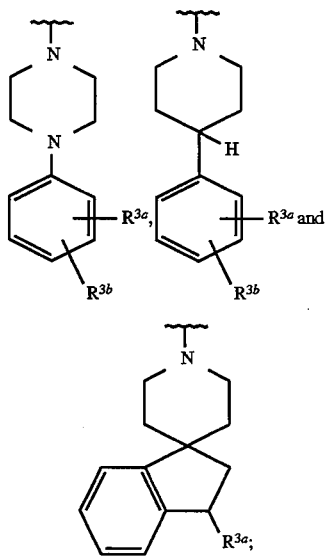

$R^{3a}$ and $R^{3b}$ are independently selected from the group consisting of: hydrogen, $C_1$–$C_6$ alkyl, halogen, —$OR^2$, —$OR^6$, —$NHSO_2CF_3$, —$(CH_2)_rOR^6$, —$(CH_2)_rN(R^2)$ $(R^6)$, —$(CH_2)_r(R^6)$, —$(CH_2)_rC(O)OR^2$, —$(CH_2)_rC(O)$ $OR^6$, —$(CH_2)_rOC(O)R^2$, —$(CH_2)_rOC(O)R^6$, —$(CH_2)_r$ $C(O)R^2$, —$(CH_2)_rC(O)R^6$, —$(CH_2)_rC(O)N(R^2)(R^2)$, —$(CH_2)_rC(O)N(R^2)(R^6)$, —$(CH_2)_rN(R^2)C(O)R^2$, —$(CH_2)_rN(R^2)C(O)R^6$, —$(CH_2)_rN(R^6)C(O)R^2$, —$(CH_2)_rN(R^6)C(O)R^6$, —$(CH_2)_rN(R^2)C(O)OR^2$, —$(CH_2)_rN(R^2)C(O)OR^6$, —$(CH_2)_rN(R^6)C(O)OR^2$, —$(CH_2)_rN(R^6)C(O)OR^6$, —$(CH_2)_rN(R^2)C(O)N(R^2)$ $(R^6)$, —$(CH_2)_rN(R^2)C(O)N(R^2)(R^2)$, —$(CH_2)_rN(R^6)C$ $(O)N(R^2)(R^6)$, —$(CH_2)_rN(R^2)SO_2R^6$, —$(CH_2)_rN(R^2)$ $SO_2R^2$, —$(CH_2)_rN(R^6)SO_2R^2$, —$(CH_2)_rN(R^6)SO_2R^6$, —$(CH_2)_rOC(O)N(R^2)(R^6)$, —$(CH_2)_rOC(O)N(R^2)$ $(R^2)$, —$(CH_2)_rSO_2N(R^2)(R^6)$, —$(CH_2)_rSO_2N(R^2)$ $(R^2)$, —$(CH_2)_rSO_2NHC(O)R^6$, —$(CH_2)_rSO_2NHC(O)$ $R^2$, —$(CH_2)_rSO_2NHC(O)OR^6$, —$(CH_2)_rSO_2NHC(O)$ $OR^2$, —$(CH_2)_rC(O)NHC(O)N(R^2)(R^6)$, —$(CH_2)_rC(O)$ $NHC(O)N(R^2)(R^2)$, —$(CH_2)_rC(O)NHC(O)R^6$, —$(CH_2)_rCONHC(O)R^2$, —$(CH_2)_rCONHSO_2R^6$, —$(CH_2)_rCONHSO_2R^2$, —$(CH_2)_rCONHSO_2N(R^2)$ $(R^2)$, —$(CH_2)_rCONHSO_2N(R^2)(R^6)$, —$(CH_2)_rN(R^2)$ $SO_2N(R^2)(R^6)$, —$(CH_2)_rN(R^6)SO_2N(R^2)(R^6)$, —$(CH_2)_rS(O)_mR^6$, and —$(CH_2)_rS(O)_mR^2$;

Y is —$SO_2$— or —$C(O)$—;

$R^2$ is selected from: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur or $NR^{2a}$;

$R^{2a}$ is hydrogen, or $C_1$–$C_6$ alkyl optionally substituted by hydroxyl;

$R^4$ and $R^5$ are independently hydrogen, $C_1$–$C_6$ alkyl, substituted $C_1$–$C_6$ alkyl where the substituents are 1 to 5 halo, 1 to 3 hydroxy, 1 to 3 $C_1$–$C_{10}$ alkanoyloxy, 1 to 3 $C_1$–$C_6$ alkoxy, phenyl, phenoxy, 2-furyl, $C_1$–$C_6$ alkoxycarbonyl, or $S(O)_m(C_1$–$C_6$ alkyl); or $R^4$ and $R^5$ can be taken together to form —$(CH_2)_dL_a(CH_2)_e$— where $L_a$ is $C(R^2)_2$, O, $S(O)_m$ or $N(R^2)$, d and e are independently 1 to 3 and $R^2$ is as defined above;

A is:

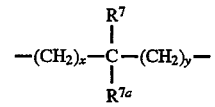

where x and y are independently 0, 1, 2 or 3;

$R^6$ is hydrogen, $C_1$–$C_6$ alkyl, or $(CH_2)_v$aryl, wherein the alkyl and $(CH_2)_v$ groups may be optionally substituted by 1–2 $O(R^2)$, $S(O)_mR^2$, 1H-tetrazol-5-yl, $C(O)OR^2$, $C(O)N(R^2)(R^2)$, $SO_2N(R^2)(R^2)$, or $N(R^2)C(O)N(R^2)$ $(R^2)$, and where aryl is phenyl, naphthyl, pyridyl, 1H-tetrazol-5-yl, triazolyl, imidazolyl, indolyl, thiazolyl, pyrazolyl, thiadiazolyl, imidazolone-1-yl, oxadiazolyl, benzimidazol-2-yl, or triazolinone-yl, optionally substituted with $C_1$–$C_6$ alkyl, $C_3$–$C_6$ cycloalkyl, amino, or hydroxyl;

$R^7$ and $R^{7a}$ are independently hydrogen, $C_1$–$C_6$ alkyl, trifluoromethyl, phenyl, or substituted $C_1$–$C_6$ alkyl where the substituents are imidazolyl, phenyl, naphthyl, indolyl, p-hydroxyphenyl, $OR^2$, $S(O)_mR^2$, $C(O)OR^2$, $C_3$–$C_7$ cycloalkyl, $N(R^2)(R^2)$, or $C(O)N(R^2)$ $(R^2)$; or $R^7$ and $R^{7a}$ can independently be joined to one or both of $R^4$ and $R^5$ groups to form an alkylene bridge between the terminal nitrogen and the alkyl portion of the $R^7$ or $R^{7a}$ groups, wherein the alkylene bridge contains 1 to 5 carbons atoms; or $R^7$ and $R^{7a}$ can be joined to one another to form a $C_3$–$C_7$ cycloalkyl;

m is 0, 1, or 2;

r is 0, 1, 2, or 3;

v is 0, 1, or 2;

and pharmaceutically acceptable salts and individual diastereomers thereof;

and an additional growth hormone secretagogue.

2. The composition of claim 1 wherein the additional growth hormone secretagogue is selected from the group

37 consisting of: growth hormone releasing peptide GHRP-6; growth hormone releasing peptide GHRP-2; growth hormone releasing peptide GHRP-1; hexarelin; B-HT920; growth hormone releasing factor; IGF-1; and IGF-2.

3. A method for increasing levels of endogenous growth hormone in a human or an animal which comprises administering to such human or animal an effective amount of a compound of the Formula I:

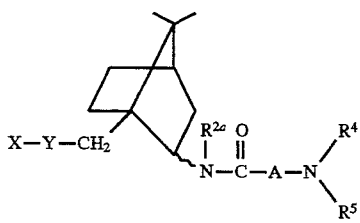

Formula I wherein:

X is selected from the group consisting of:

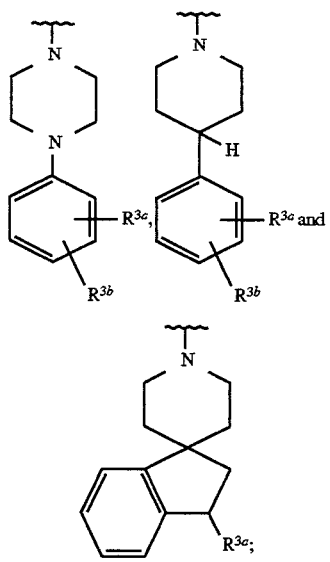

$R^{3a}$ and $R^{3b}$ are independently selected from the group consisting of: hydrogen, $C_1$–$C_6$ alkyl, halogen —$OR^2$, —$OR^6$, —$NHSO_2CF_3$, —$(CH_2)_rOR^6$, —$(CH_2)_rN(R^2)$ $(R^6)$, —$(CH_2)_rR^6$, —$(CH_2)_rC(O)OR^2$, —$(CH_2)_rC(O)$ $OR^6$, —$(CH_2)_rOC(O)R^2$, —$(CH_2)_rOC(O)R^6$, —$(CH_2)$ $_rC(O)R^2$, —$(CH_2)_rC(O)R^6$, —$(CH_2)_rC(O)N(R^2)(R^2)$, —$(CH_2)_rC(O)N(R^2)(R^6)$, —$(CH_2)_rN(R^2)C(O)R^2$, —$(CH_2)_rN(R^2)C(O)R^6$, —$(CH_2)_rN(R^6)C(O)R^2$, —$(CH_2)_rN(R^6)C(O)R^6$, —$(CH_2)_rN(R^2)C(O)OR^2$, —$(CH_2)_rN(R^2)C(O)OR^6$, —$(CH_2)_rN(R^6)C(O)OR^2$, —$(CH_2)_rN(R^6)C(O)OR^6$, —$(CH_2)_rN(R^2)C(O)N(R^2)$ $(R^6)$, —$(CH_2)_rN(R^2)C(O)N(R^2)(R^2)$, —$(CH_2)_rN(R^6)C$ $(O)N(R^2)(R^6)$, —$(CH_2)_rN(R^2)SO_2R^6$, —$(CH_2)_rN(R^2)$ $SO_2R^2$, —$(CH_2)_rN(R^6)SO_2R^2$, —$(CH_2)_rN(R^6)SO_2R^6$, —$(CH_2)_rOC(O)N(R^2)(R^6)$, —$(CH_2)_rOC(O)N(R^2)$ $(R^2)$, —$(CH_2)_rSO_2N(R^2)(R^6)$, —$(CH_2)_rSO_2N(R^2)$ $(R^2)$, —$(CH_2)_rSO_2NHC(O)R^6$, —$(CH_2)_rSO_2NHC(O)$ $R^2$, —$(CH_2)_rSO_2NHC(O)OR^6$, —$(CH_2)_rSO_2NHC(O)$ $OR^2$, —$(CH_2)_rC(O)NHC(O)N(R^2)(R^6)$, —$(CH_2)_rC(O)$

38

$NHC(O)N(R^2)(R^2)$, —$(CH_2)_rC(O)NHC(O)R^6$, —$(CH_2)_rCONHC(O)R^2$, —$(CH_2)_rCONHSO_2R^6$, —$(CH_2)_rCONHSO_2R^2$, —$(CH_2)_rCONHSO_2N(R^2)$ $(R^2)$, —$(CH_2)_rCONHSO_2N(R^2)(R^6)$, —$(CH_2)_rN(R^2)$ $SO_2N(R^2)(R^6)$, —$(CH_2)_rN(R^6)SO_2N(R^2)(R^6)$, —$(CH_2)_rS(O)_mR^6$, and —$(CH_2)_rS(O)_mR^2$;

Y is —$SO_2$— or —$C(O)$—;

$R^2$ is selected from: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur or $NR^{2a}$;

$R^{2a}$ is hydrogen, or $C_1$–$C_6$ alkyl optionally substituted by hydroxyl;

$R^4$ and $R^5$ are independently hydrogen, $C_1$–$C_6$ alkyl, substituted $C_1$–$C_6$ alkyl where the substituents are 1 to 5 halo, 1 to 3 hydroxy, 1 to 3 $C_1$–$C_{10}$ alkanoyloxy, 1 to 3 $C_1$–$C_6$ alkoxy, phenyl, phenoxy, 2-furyl, $C_1$–$C_6$ alkoxycarbonyl, or $S(O)_m(C_1$–$C_6$ alkyl); or $R^4$ and $R^5$ can be taken together to form —$(CH_2)_dL_a(CH_2)_e$— where $L_a$ is $C(R^2)_2$, O, $S(O)_m$ or $N(R^2)$, d and e are independently 1 to 3 and $R^2$ is as defined above;

A is:

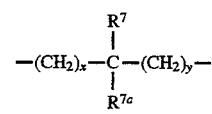

where x and y are independently 0, 1, 2 or 3;

$R^6$ is hydrogen, $C_1$–$C_6$ alkyl, or $(CH_2)_v$aryl, wherein the alkyl and $(CH_2)_v$ groups may be optionally substituted by 1–2 $O(R^2)$, $S(O)_mR^2$, 1H-tetrazol-5-yl, $C(O)OR^2$, $C(O)N(R^2)(R^2)$, $SO_2N(R^2)(R^2)$, or $N(R^2)C(O)N(R^2)$ $(R^2)$, and where aryl is phenyl, naphthyl, pyridyl, 1H-tetrazol-5-yl, triazolyl, imidazolyl, indolyl, thiazolyl, pyrazolyl, thiadiazolyl, imidazolone-1-yl, oxadiazolyl, benzimidazol-2-yl, or triazolinone-yl, optionally substituted with $C_1$–$C_6$ alkyl, $C_3$–$C_6$ cycloalkyl, amino, or hydroxyl;

$R^7$ and $R^{7a}$ are independently hydrogen, $C_1$–$C_6$ alkyl, trifluoromethyl, phenyl, or substituted $C_1$–$C_6$ alkyl where the substituents are imidazolyl, phenyl, naphthyl, indolyl, p-hydroxyphenyl, $OR^2$, $S(O)_mR^2$, $C(O)OR^2$, $C_3$–$C_7$ cycloalkyl, $N(R^2)(R^2)$, or $C(O)N(R^2)$ $(R^2)$; or $R^7$ and $R^{7a}$ can independently be joined to one or both of $R^4$ and $R^5$ groups to form an alkylene bridge between the terminal nitrogen and the alkyl portion of the $R^7$ or $R^{7a}$ groups, wherein the alkylene bridge contains 1 to 5 carbons atoms; or $R^7$ and $R^{7a}$ can be joined to one another to form a $C_3$–$C_7$ cycloalkyl;

m is 0, 1, or 2;

r is 0, 1, 2, or 3;

v is 0, 1, or 2;

and pharmaceutically acceptable salts and individual diastereomers thereof.

4. The method of claim 3 wherein the compound of Formula I:

39

X is selected from the group consisting of:

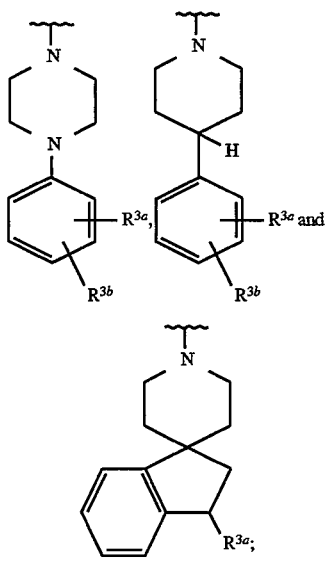

$R^{3a}$ and $R^{3b}$ are independently selected from the group consisting of: hydrogen, $C_1-C_6$ alkyl, halogen, —$OR^2$, —$OR^6$, —$(CH_2)_v(R^6)$, —$(CH_2)_vC(O)OR^2$, —$(CH_2)_vC(O)OR^6$, —$(CH_2)_vC(O)N(R^2)(R^2)$, —$(CH_2)_vC(O)N(R^2)(R^6)$, —$(CH_2)_vN(R^2)C(O)R^2$, —$(CH_2)_vN(R^2)C(O)R^6$, —$(CH_2)_vN(R^6)C(O)R^2$, —$(CH_2)_vN(R^6)C(O)R^6$, —$(CH_2)_vN(R^2)C(O)OR^2$, —$(CH_2)_vN(R^2)C(O)N(R^2)(R^6)$, —$(CH_2)_vN(R^2)C(O)N(R^2)(R^2)$, —$(CH_2)_vN(R^6)C(O)N(R^2)(R^6)$, —$(CH_2)_vS(O)_mR^6$, and —$(CH_2)_vS(O)_mR^2$;

$R^2$ is hydrogen, $C_1-C_6$ alkyl, or $C_3-C_7$ cycloalkyl and where two $C_1-C_6$ alkyl groups are present on one atom they may be optionally joined to form a $C_4-C_7$ cyclic ring optionally including oxygen, sulfur or $NR^{2a}$;

$R^{2a}$ is hydrogen or $C_1-C_6$ alkyl, optionally substituted by hydroxyl;

$R^4$ and $R^5$ are independently hydrogen, $C_1-C_6$ alkyl, or substituted $C_1-C_6$ alkyl where the substituents are 1 to 5 halo, 1 to 3 hydroxyl, $S(O)_m(C_1-C_6$ alkyl) or phenyl;

$R^6$ is H, $C_1-C_6$ alkyl, or $(CH_2)_v$aryl, wherein the $(CH_2)_v$ and alkyl groups may be optionally substituted by 1–2 $O(R^2)$, $S(O)_mR^2$, $C(O)OR^2$, $C(O)N(R^2)(R^2)$, $SO_2N(R^2)(R^2)$ or $N(R^2)C(O)N(R^2)(R^2)$, wherein the aryl group is selected from: phenyl, naphthyl, indolyl, pyridyl, 1H-tetrazol-5-yl, triazolyl, imidazolyl, thiazolyl, oxadiazolyl, pyrazolyl, thiadiazolyl, and benzimidazol-2-yl, which are optionally substituted with $C_1-C_6$ alkyl, $C_3-C_6$ cycloalkyl, amino, or hydroxyl;

A is:

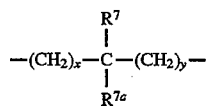

where x and y are independently 0, 1, or 2;

$R^7$ and $R^{7a}$ are independently hydrogen, $C_1-C_6$ alkyl, trifluoromethyl, phenyl, or substituted $C_1-C_6$ alkyl where the substituents are imidazolyl, phenyl, naphthyl, indolyl, p-hydroxyphenyl, $OR^2$, $S(O)_mR^2$, $C(O)OR^2$, $C_5-C_7$ cycloalkyl, $N(R^2)(R^2)$, or $C(O)N(R^2)(R^2)$; or $R^7$ and $R^{7a}$ can independently be joined to one

40 of $R^4$ or $R^5$ to form an alkylene bridge between the terminal nitrogen and the alkyl portion of $R^7$ or $R^{7a}$ groups to form 5 or 6 membered rings; or $R^7$ and $R^{7a}$ can be joined to one another to form a $C_3$ cycloalkyl;

m is 0, 1, or 2;

r is 0, 1, 2, or 3;

v is 0, 1, or 2;

and pharmaceutically acceptable salts and individual diastereomers thereof.

5. A method for the treatment of a disease or a condition which is benefited by the anabolic effects of enhanced growth hormone levels that comprises administering to a patient in need thereof an effective amount a compound of Formula I:

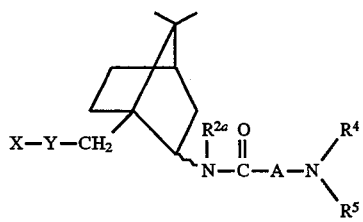

Formula I wherein:

X is selected from the group consisting of:

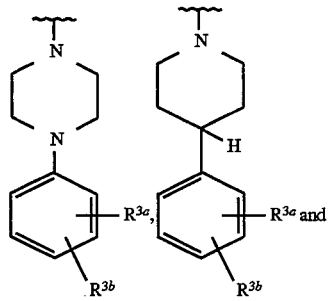

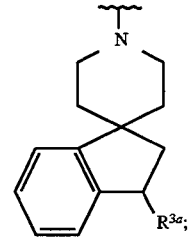

$R^{3a}$ and $R^{3b}$ are independently selected from the group consisting of: hydrogen, $C_1-C_6$ alkyl, halogen, —$OR^2$, —$OR^6$, —$NHSO_2CF_3$, —$(CH_2)_rOR^6$, —$(CH_2)_rN(R^2)(R^6)$, —$(CH_2)_r(R^6)$, —$(CH_2)_rC(O)OR^2$, —$(CH_2)_rC(O)OR^6$, —$(CH_2)_rOC(O)R^2$, —$(CH_2)_rOC(O)R^6$, —$(CH_2)_rC(O)R^2$, —$(CH_2)_rC(O)R^6$, —$(CH_2)_rC(O)N(R^2)(R^2)$, —$(CH_2)_rC(O)N(R^2)(R^6)$, —$(CH_2)_rN(R^2)C(O)R^2$, —$(CH_2)_rN(R^2)C(O)R^6$, —$(CH_2)_rN(R^6)C(O)R^2$, —$(CH_2)_rN(R^6)C(O)R^6$, —$(CH_2)_rN(R^2)C(O)OR^2$, —$(CH_2)_rN(R^2)C(O)OR^6$, —$(CH_2)_rN(R^6)C(O)OR^2$, —$(CH_2)_rN(R^6)C(O)OR^6$, —$(CH_2)_rN(R^2)C(O)N(R^2)(R^6)$, —$(CH_2)_rN(R^2)C(O)N(R^2)(R^2)$, —$(CH_2)_rN(R^6)C(O)N(R^2)(R^6)$, —$(CH_2)_rN(R^2)SO_2R^6$, —$(CH_2)_rN(R^2)SO_2R^2$, —$(CH_2)_rN(R^6)SO_2R^2$, —$(CH_2)_rN(R^6)SO_2R^6$, —$(CH_2)_rOC(O)N(R^2)(R^6)$, —$(CH_2)_rOC(O)N(R^2)(R^2)$, —$(CH_2)_rSO_2N(R^2)(R^6)$, —$(CH_2)_rSO_2N(R^2)(R^2)$, —$(CH_2)_rSO_2NHC(O)R^6$, —$(CH_2)_rSO_2NHC(O)R^2$, —$(CH_2)_rSO_2NHC(O)OR^6$, —$(CH_2)_rSO_2NHC(O)

OR², —(CH₂)ᵣC(O)NHC(O)N(R²)(R⁶), —(CH₂)ᵣC(O)
NHC(O)N(R²)(R²), —(CH₂)ᵣC(O)NHC(O)R⁶,
—(CH₂)ᵣCONHC(O)R², —(CH₂)ᵣCONHSO₂R⁶,
—(CH₂)ᵣCONHSO₂R², —(CH₂)ᵣCONHSO₂N(R²)
(R²), —(CH₂)ᵣCONHSO₂N(R²)(R⁶), —(CH₂)ᵣN(R²)
SO₂N(R²)(R⁶), —(CH₂)ᵣN(R⁶)SO₂N(R²)(R⁶),
—(CH₂)ᵣS(O)ₘR⁶, and —(CH₂)ᵣS(O)ₘR²;

Y is —SO₂— or —C(O)—;

R² is selected from: hydrogen, C₁-C₆ alkyl, and C₃-C₇ cycloalkyl, and where two C₁-C₆ alkyl groups are present on one atom, they may be optionally joined to form a C₃-C₈ cyclic ring, optionally including oxygen, sulfur or NR²ᵃ;

R²ᵃ is hydrogen, or C₁-C₆ alkyl optionally substituted by hydroxyl;

R⁴ and R⁵ are independently hydrogen, C₁-C₆ alkyl, substituted C₁-C₆ alkyl where the substituents are 1 to 5 halo, 1 to 3 hydroxy, 1 to 3 C₁-C₁₀ alkanoyloxy, 1 to 3 C₁-C₆ alkoxy, phenyl, phenoxy, 2-furyl, C₁-C₆ alkoxycarbonyl, or S(O)ₘ(C₁-C₆ alkyl); or R⁴ and R⁵ can be taken together to form —(CH₂)ₐLₐ(CH₂)ₑ— where Lₐ is C(R²)₂, O, S(O)ₘ or N(R²), d and e are independently 1 to 3 and R² is as defined above;

A is:

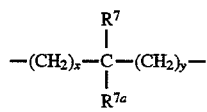

where x and y are independently 0, 1, 2 or 3;

R⁶ is hydrogen, C₁-C₆ alkyl, or (CH₂)ᵥaryl, wherein the alkyl and (CH₂)ᵥ groups may be optionally substituted by 1-2 O(R²), S(O)ₘR², 1H-tetrazol-5-yl, C(O)OR², C(O)N(R²)(R²), SO₂N(R²)(R²), or N(R²)C(O)N(R²) (R²), and where aryl is phenyl, naphthyl, pyridyl, 1H-tetrazol-5-yl, triazolyl, imidazolyl, indolyl, thiazolyl, pyrazolyl, thiadiazolyl, imidazolone-1-yl, oxadiazolyl, benzimidazol-2-yl, or triazolinone-yl, optionally substituted with C₁-C₆ alkyl, C₃-C₆ cycloalkyl, amino, or hydroxyl;

R⁷ and R⁷ᵃ are independently hydrogen, C₁-C₆ alkyl, trifluoromethyl, phenyl, or substituted C₁-C₆ alkyl where the substituents are imidazolyl, phenyl, naphthyl, indolyl, p-hydroxyphenyl, OR², S(O)ₘR², C(O)OR², C₃-C₇ cycloalkyl, N(R²)(R²), or C(O)N(R²) (R²); or R⁷ and R⁷ᵃ can independently be joined to one or both of R⁴ and R⁵ groups to form an alkylene bridge between the terminal nitrogen and the alkyl portion of the R⁷ or R⁷ᵃ groups, wherein the alkylene bridge contains 1 to 5 carbons atoms; or R⁷ and R⁷ᵃ can be joined to one another to form a C₃-C₇ cycloalkyl;

m is 0, 1, or 2;

r is 0, 1, 2, or 3;

v is 0, 1, or 2;

and pharmaceutically acceptable salts and individual diastereomers thereof.

6. The method of claim 5 wherein the compound of Formula I:

X is selected from the group consisting of:

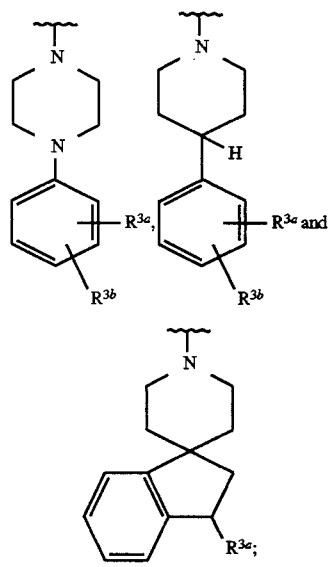

R³ᵃ and R³ᵇ are independently selected from the group consisting of: hydrogen, C₁-C₆ alkyl, halogen, —OR², —OR⁶, —(CH₂)ᵣ(R⁶), —(CH₂)ᵣC(O)OR², —(CH₂)ᵣC (O)OR⁶, —(CH₂)ᵣC(O)N(R²)(R²), —(CH₂)ᵣC(O)N (R²)(R⁶), —(CH₂)ᵣN(R²)C(O)R², —(CH₂)ᵣN(R²)C(O) R⁶, —(CH₂)ᵣN(R⁶)C(O)R², —(CH₂)ᵣN(R⁶)C(O)R⁶, —(CH₂)ᵣN(R²)C(O)OR², —(CH₂)ᵣN(R²)C(O)N(R²) (R⁶), —(CH₂)ᵣN(R²)C(O)N(R²)(R²), —(CH₂)ᵣN(R⁶)C (O)N(R²)(R⁶), —(CH₂)ᵣS(O)ₘR⁶, and —(CH₂)ᵣS(O)ₘR²;

R² is hydrogen, C₁-C₆ alkyl, or C₃-C₇ cycloalkyl and where two C₁-C₆ alkyl groups are present on one atom they may be optionally joined to form a C₄-C₇ cyclic ring optionally including oxygen, sulfur or NR²ᵃ;

R²ᵃ is hydrogen or C₁-C₆ alkyl, optionally substituted by hydroxyl;

R⁴ and R⁵ are independently hydrogen, C₁-C₆ alkyl, or substituted C₁-C₆ alkyl where the substituents are 1 to 5 halo, 1 to 3 hydroxyl, S(O)ₘ(C₁-C₆ alkyl) or phenyl;

R⁶ is H, C₁-C₆ alkyl, or (CH₂)ᵥaryl, wherein the (CH₂)ᵥ and alkyl groups may be optionally substituted by 1-2 O(R²), S(O)ₘR², C(O)OR², C(O)N(R²)(R²), SO₂N(R²) (R²) or N(R²)C(O)N(R²)(R²), wherein the aryl group is selected from: phenyl, naphthyl, indolyl, pyridyl, 1H-tetrazol-5-yl, triazolyl, imidazolyl, thiazolyl, oxadiazolyl, pyrazolyl, thiadiazolyl, and benzimidazol-2-yl, which are optionally substituted with C₁-C₆ alkyl, C₃-C₆ cycloalkyl, amino, or hydroxyl;

A is:

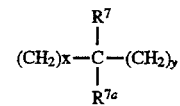

where x and y are independently 0, 1, or 2;

R⁷ and R⁷ᵃ are independently hydrogen, C₁-C₆ alkyl, trifluoromethyl, phenyl, or substituted C₁-C₆ alkyl where the substituents are imidazolyl, phenyl, naphthyl, indolyl, p-hydroxyphenyl, OR², S(O)ₘR², C(O)OR², C₅-C₇ cycloalkyl, N(R²)(R²), or C(O)N(R²) (R²); or R⁷ and R⁷ᵃ can independently be joined to one of $R^4$ or $R^5$ to form an alkylene bridge between the terminal nitrogen and the alkyl portion of $R^7$ or $R^{7a}$ groups to form 5 or 6 membered rings; or $R^7$ and $R^{7a}$ can be joined to one another to form a $C_3$ cycloalkyl;

m is 0, 1, or 2;

r is 0, 1, 2, or 3;

v is 0, 1, or 2;

and pharmaceutically acceptable salts and individual diastereomers thereof.

7. The method of claim 5 wherein the compound is selected from the group consisting of:

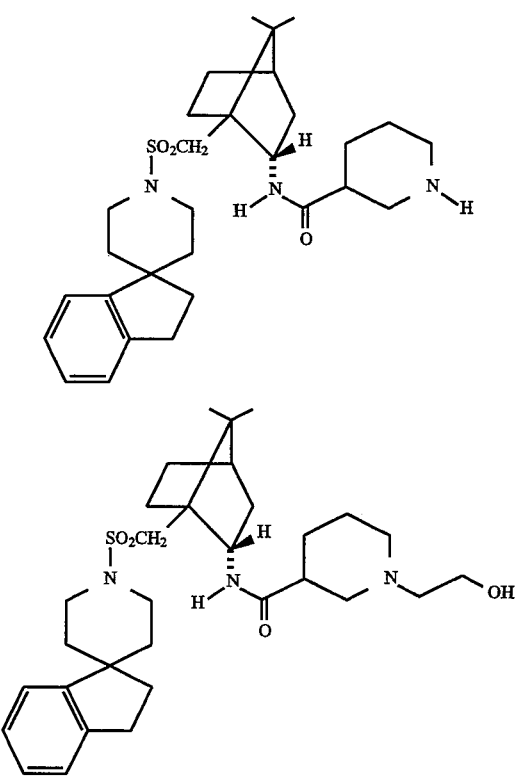

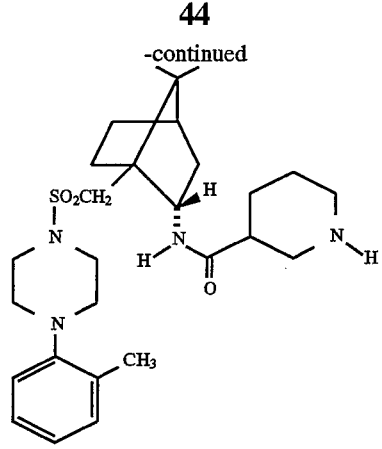

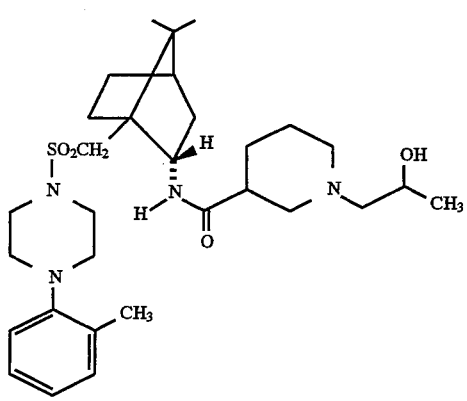

and their pharmaceutically acceptable salts and individual diastereomers thereof where not otherwise specified.

8. The method of claim 5 wherein the disease or condition is selected from the group consisting of: osteoporosis; catabolic illness; immune deficiency; hip fracture; musculoskeletal impairment in the elderly; growth hormone deficiency in adults or in children; obesity; cachexia and protein loss due to chronic illness; and the treatment of patients recovering from major surgery, wounds or burns.

* * * * *